United States Patent
Harayama et al.

(10) Patent No.: US 7,662,551 B2
(45) Date of Patent: Feb. 16, 2010

(54) SYNTHESIS OF HYBRID POLYNUCLEOTIDE MOLECULES USING SINGLE-STRANDED POLYNUCLEOTIDE MOLECULES

(75) Inventors: Shigeaki Harayama, Tokyo (JP); Kouhei Ohnishi, Kochi (JP); Miho Kikuchi, Kamaishi (JP)

(73) Assignee: Alligator Bioscience AB, Lund (SE)

( * ) Notice: Subject to any disclaimer, the term of this patent is extended or adjusted under 35 U.S.C. 154(b) by 507 days.

(21) Appl. No.: 10/299,362

(22) Filed: Nov. 18, 2002

(65) Prior Publication Data

US 2003/0138825 A1  Jul. 24, 2003

Related U.S. Application Data

(63) Continuation of application No. 09/742,123, filed on Dec. 22, 2000, now abandoned.

(51) Int. Cl.
- C12Q 1/68 (2006.01)
- C12P 19/34 (2006.01)
- C12N 15/00 (2006.01)
- C07H 21/02 (2006.01)
- C07H 21/04 (2006.01)

(52) U.S. Cl. .................. 435/6; 435/91.1; 435/91.2; 435/320.1; 536/23.1; 536/24.3; 536/24.33

(58) Field of Classification Search .............. 435/6, 435/91.1, 183, 320.1, 455, 462, 468, 91.2; 436/94; 536/23.1, 24.3, 24.33, 25.3

See application file for complete search history.

(56) References Cited

U.S. PATENT DOCUMENTS

| | | |
|---|---|---|
| 4,683,202 A | 7/1987 | Mullis et al. |
| 4,888,286 A | 12/1989 | Crea |
| 4,965,188 A | 10/1990 | Mullis et al. |
| 4,994,368 A | 2/1991 | Goodman et al. |
| 5,023,171 A | 6/1991 | Ho et al. |

(Continued)

FOREIGN PATENT DOCUMENTS

EP    0 368 684 A    5/1990

(Continued)

OTHER PUBLICATIONS

Attached one of definitions for "cloning".*

(Continued)

*Primary Examiner*—Frank W Lu
(74) *Attorney, Agent, or Firm*—Dann, Dorfman, Herrell & Skillman; Robert C. Netter

(57) ABSTRACT

A method to make libraries of hybrid polynucleotide molecules of two parental polynucleotide molecules utilizing single-stranded DNA was invented. Example of the method comprises several steps: (i) preparation of two single-stranded polynucleotide molecules comprising sequences containing one or more parts of homology and one or more parts of heterology, (ii) random or non-random fragmentation of said polynucleotides, (iii) hybridization of the fragmented molecules followed by de novo polynucleotide synthesis (i.e. polynucleotide chain elongation) on the hybridized molecules, (iv) separation of the chain elongation products (i.e. double-stranded polynucleotide molecules) into single-stranded polynucleotide molecules (denaturation) (v) hybridization of the resultant single-stranded polynucleotide molecules followed by de novo polynucleotide synthesis on the hybridized molecules, and (vi) repeating at least two further cycles of steps (iv) and (v).

13 Claims, 6 Drawing Sheets

U.S. PATENT DOCUMENTS

| | | | |
|---|---|---|---|
| 5,043,272 A | 8/1991 | Hartley |
| 5,223,408 A | 6/1993 | Goeddel et al. |
| 5,252,479 A | 10/1993 | Srivastava |
| 5,270,170 A | 12/1993 | Schatz et al. |
| 5,338,665 A | 8/1994 | Schatz et al. |
| 5,491,074 A | 2/1996 | Aldwin et al. |
| 5,498,530 A | 3/1996 | Schatz et al. |
| 5,502,167 A | 3/1996 | Waldmann et al. |
| 5,512,463 A | 4/1996 | Stemmer |
| 5,514,568 A | 5/1996 | Stemmer |
| 5,521,291 A | 5/1996 | Curiel et al. |
| 5,573,907 A | 11/1996 | Carrino et al. |
| 5,605,793 A | 2/1997 | Stemmer |
| 5,712,089 A | 1/1998 | Borrebaeck et al. |
| 5,714,316 A | 2/1998 | Weiner et al. |
| 5,723,323 A | 3/1998 | Kauffman et al. |
| 5,733,731 A | 3/1998 | Schatz et al. |
| 5,733,753 A | 3/1998 | Jørgensen |
| 5,763,192 A | 6/1998 | Kauffman et al. |
| 5,798,208 A | 8/1998 | Crea |
| 5,811,238 A | 9/1998 | Stemmer et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,830,650 A | 11/1998 | Crea |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minshull et al. |
| 5,858,657 A | 1/1999 | Winter et al. |
| 5,858,725 A | 1/1999 | Crowe et al. |
| 5,871,907 A | 2/1999 | Winter et al. |
| 5,925,544 A | 7/1999 | Jørgensen |
| 5,928,905 A | 7/1999 | Stemmer et al. |
| 5,939,250 A | 8/1999 | Short |
| 5,965,408 A | 10/1999 | Short |
| 5,969,108 A | 10/1999 | McCafferty et al. |
| 5,976,862 A | 11/1999 | Kauffman et al. |
| 6,096,548 A | 8/2000 | Stemmer |
| 6,117,679 A | 9/2000 | Stemmer |
| 6,132,970 A | 10/2000 | Stemmer |
| 6,143,527 A | 11/2000 | Pachuk et al. |
| 6,153,410 A | 11/2000 | Arnold et al. |
| 6,156,511 A | 12/2000 | Schatz et al. |
| 6,159,687 A | 12/2000 | Vind |
| 6,159,688 A | 12/2000 | Borchert et al. |
| 6,159,690 A | 12/2000 | Borrebaeck et al. |
| 6,165,793 A | 12/2000 | Stemmer |
| 6,177,263 B1 | 1/2001 | Arnold et al. |
| 6,180,406 B1 | 1/2001 | Stemmer |
| 6,355,484 B1 * | 3/2002 | Patten et al. ......... 435/440 |
| 6,368,861 B1 * | 4/2002 | Crameri et al. ......... 435/440 |
| 6,413,774 B1 | 7/2002 | Stemmer et al. |
| 2004/0048268 A1 | 3/2004 | Delcourt et al. |

FOREIGN PATENT DOCUMENTS

| | | |
|---|---|---|
| EP | 0 415 731 A | 3/1991 |
| EP | 0415731 | 3/1991 |
| EP | 0 456 304 A | 11/1991 |
| EP | 0557897 | 9/1993 |
| EP | 0 590 689 A | 4/1994 |
| EP | 0911396 | 4/1999 |
| EP | 0552266 | 1/2000 |
| FR | 2813314 | 3/2002 |
| GB | 9712512.4 | 6/1997 |
| JP | 10-66576 | 3/1998 |
| JP | 2000-308490 A | 11/2001 |
| WO | WO 86/05803 | 10/1986 |
| WO | 9007936 | 7/1990 |
| WO | WO 90/07936 | 7/1990 |
| WO | 9014430 | 11/1990 |
| WO | WO 90/14430 | 11/1990 |
| WO | WO 91/07506 | 5/1991 |
| WO | 9116427 | 10/1991 |
| WO | WO 91/15581 | 10/1991 |
| WO | WO 91/16427 | 10/1991 |
| WO | WO 92/01047 | 1/1992 |
| WO | 9207075 | 4/1992 |
| WO | WO 92/07075 | 4/1992 |
| WO | WO 92/15702 | 9/1992 |
| WO | WO 92/18645 | 10/1992 |
| WO | 9302191 | 2/1993 |
| WO | 9307282 | 4/1993 |
| WO | WO 93/06213 | 4/1993 |
| WO | WO 93/07282 | 4/1993 |
| WO | WO 93/08278 | 4/1993 |
| WO | 9311237 | 6/1993 |
| WO | WO 93/12257 | 6/1993 |
| WO | 9315208 | 8/1993 |
| WO | 9316192 | 8/1993 |
| WO | 9319172 | 9/1993 |
| WO | 9409817 | 5/1994 |
| WO | 9413804 | 6/1994 |
| WO | WO 94/12632 | 6/1994 |
| WO | WO 94/24313 | 10/1994 |
| WO | WO 94/28173 | 12/1994 |
| WO | WO 95/22625 | 8/1995 |
| WO | WO 96/05803 | 2/1996 |
| WO | WO 96/17056 | 6/1996 |
| WO | WO 96/40750 | 12/1996 |
| WO | WO 96/40987 | 12/1996 |
| WO | WO 97/07205 | 2/1997 |
| WO | WO 97/07206 | 2/1997 |
| WO | WO 97/08320 | 3/1997 |
| WO | 9720078 | 6/1997 |
| WO | WO 97/20078 | 6/1997 |
| WO | WO 97/35957 | 10/1997 |
| WO | WO 97/35966 | 10/1997 |
| WO | WO 98/01581 | 1/1998 |
| WO | WO 98/05765 | 2/1998 |
| WO | WO 98/13485 | 4/1998 |
| WO | WO 98/13487 | 4/1998 |
| WO | WO 98/25965 | 6/1998 |
| WO | WO 98/27230 | 6/1998 |
| WO | 9832845 | 7/1998 |
| WO | WO 98/28416 | 7/1998 |
| WO | WO 98/31837 | 7/1998 |
| WO | WO 98/32845 | 7/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | 9858080 | 12/1998 |
| WO | WO 98/58080 | 12/1998 |
| WO | WO 99/21979 | 5/1999 |
| WO | WO 99/23107 | 5/1999 |
| WO | WO 99/23236 | 5/1999 |
| WO | WO 99/33965 | 7/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45110 | 9/1999 |
| WO | WO 99/57128 | 11/1999 |
| WO | WO 99/58661 | 11/1999 |
| WO | WO 99/65927 | 12/1999 |
| WO | WO 00/04190 | 1/2000 |
| WO | WO 00/09679 | 2/2000 |
| WO | WO 00/09727 | 2/2000 |
| WO | WO 00/12680 | 3/2000 |
| WO | WO 00/18906 | 4/2000 |
| WO | WO 00/20573 | 4/2000 |
| WO | WO 00/28008 | 5/2000 |

| | | |
|---|---|---|
| WO | WO 00/28017 | 5/2000 |
| WO | WO 00/28018 | 5/2000 |
| WO | WO 00/34512 | 6/2000 |
| WO | WO 00/42559 | 7/2000 |
| WO | WO 00/42560 | 7/2000 |
| WO | WO 00/42561 | 7/2000 |
| WO | WO 00/46344 | 8/2000 |
| WO | WO 00/52155 | 9/2000 |
| WO | WO 00/53744 | 9/2000 |
| WO | WO 00/58517 | 10/2000 |
| WO | WO 00/61731 | 10/2000 |
| WO | WO 00/61740 | 10/2000 |
| WO | WO 00/72013 | 11/2000 |
| WO | WO 00/73433 | 12/2000 |

OTHER PUBLICATIONS

Alber, Tom, et al., "Contributions of hydrogen bonds of Thr 157 to the thermodynamic stability of phage T4 lysozyme." Nature, 330: 41-46 (1987).

Arrizubieta, Maria Jesus and Julio Polaina. "Increased Thermal Resistance and Modification of the Catalytic Properties of a β-Glucosidase by Random Mutagenesis and in Vitro Recombination." The Journal of Biological Chemistry, vol. 275, No. 37: 28843-28848 (2000).

Barbas, III, Carlos F., et al., "Assembly of combinatorial antibody libraries on phage surfaces: The gene III site." Proc. Natl. Acad. Sci., 88: 7978-7982 (1991).

Barbas, III, Carlos F., et al., "Semisynthetic combinatorial antibody libraries: A chemical solution to the diversity problem." Proc. Natl. Acad. Sci., 89: 4457-4461 (1992).

Boder, Eric T. and K. Dane Wittrup, "Yeast surface display for screening combinatorial polypeptide libraries." Nature Biotechnology, 15: 553-557 (1997).

Boublik, Yvan, et al., "Eukaryotic Virus Display: Engineering the Major Surface Glycoprotein of the *Autographa californica* Nuclear Polyhedrosis Virus (AcNPV) for the Presentation of Foreign Proteins on the Virus Surface." Bio/technology, 13: 1079-1084 (1995).

"DNA and RNA Modifying Enzymes." (Chapter 5) in Molecular Biology LabFax, ed. T. A. Brown. BIOS Scientific Publishers, Ltd. and Blackwell Scientific Publishers Ltd. (1991).

Buchholz, Christian J., et al., "In vivo selection of protease cleavage sites from retrovirus display libraries." Nature Biotechnology, 16: 951-954 (1998).

Chang, Chia-Chun J., et al., "Evolution of a cytokine using DNA family shuffling." Nature Biotechnology, 17: 793-797 (1999).

Christians, Fred C., et al., "Directed evolution of thymidine kinase for AZT phosphorylation using DNA family shuffling." Nature Biotechnology, 17: 259-264.

Crameri, Andreas and Willem P.C. Stemmer, "Combinatorial Multiple Cassette Mutagenesis Creates All the Permutations of Mutant and Wild-Type Sequences." BioTechniques, vol. 18, No. 2: 194-196 (1995).

Crameri, Andreas, et al., "DNA shuffling of a family of genes from diverse species accelerates directed evolution." Nature, 391: 288-291 (1998).

Crameri, Andreas, et al., "Molecular evolution of an arsenate detoxification pathway by DNA shuffling." Nature Biotechnology, 15: 436-438 (1997).

Dower, William J., et al., "High efficiency transformation of *E. coli* by high voltage electroporation." Nucleic Acids Research, vol. 16, No. 13: 6127-6145 (1988).

Eckstein, Fritz. "Exogenous application of ribozymes for inhibiting gene expression." Ciba Foundation Symposium, 207-217 (1997).

Ernst, Wolfgang, et al., "Baculovirus surface display: construction and screening of a eukaryotic epitope library." Nucleic Acids Research, vol. 26, No. 7: 1718-1723 (1998).

Fisch, Igor, et al., "A strategy of exon shuffling for making large peptide repertoires displayed on filamentous bacteriophage." Proc. Natl. Acad. Sci., 93: 7761-7766 (1996).

Grabherr, R., et al., "Expression of Foreign Proteins on the Surface of *Autographa californica* Nuclear Polyhedrosis Virus." BioTechniques, 22: 730-735 (1997).

Granziero, Luisa, et al., "Baculovirus cDNA libraries for expression cloning of genes encoding cell-surface antigens." Journal of Immunological Methods, 203: 131-139 (1997).

Griffiths, Andrew D., et al., "Isolation of high affinity human antibodies directly from large synthetic repertoires." Journal of Embo., 13(14): 3245-3260 (1994).

Kikuchi, Miho, et al., "An effective family shuffling method using single-stranded DNA." Gene, 243: 133-137 (2000).

Kim, Yong-Sung, et al., "Bacterial Cell Surface Display of an Enzyme Library for Selective Screening of Improved Cellulase Variants." Applied and Environmental Microbiology, vol. 66, No. 2: 788-793 (2000).

Kuipers, Oscar P., et al., "Improved site-directed mutagenesis method using PCR." Nucleic Acids Research, vol. 19, No. 16: 4558 (1991).

Larrick, James W., et al., "Rapid cloning of rearranged immunoglobulin genes from human hybridoma cells using mixed primers and the polymerase chain reaction." Biochemical and Biophysical Research Communications, vol. 160, No. 3: 1250-1256 (1989).

Leung, David W., et al., "A method for random mutagenesis of a defined DNA segment using a modified polymerase chain reaction." Technique-A Journal of Methods in Cell and Molecular Biology, vol. 1, No. 1: 11-15 (1989).

Hanahan, Douglas., "Studies on Transformation of *Escherichia coli* with Plasmids." J. Mol. Biol., 166: 557-580 (1983).

Higuchi, Kazuo, et al., "Cell display library for gene cloning of variable regions of human antibodies to hepatitis B surface antigen." Journal of Immunological Methods, 202: 193-204 (1997).

Huse, William D., et al., "Generation of a Large Combinatorial Library of the Immunoglobulin Repertoire in Phage Lambda." Science, 246: 1275-1281 (1989).

Mottershead, David, et al., "Baculoviral Display of the Green Fluorescent Protein and Rubella Virus Envelope Proteins." Biochemical and Biophysical Research Communications, 238: 717-722 (1997).

McCafferty, John, et al., "Phage antibodies: filamentous phage displaying antibody variable domains." Nature, 348: 552-554 (1990).

Marks, James D., et al., "By-Passing Immunization: Building High Affinity Human Antibodies by Chain Shuffling." Bio/Technology, 10: 779-783 (1992).

Lu, Tao and Horace B. Gray Jr., "Kinetics and mechanism of BAL 31 nuclease action on small substrates and single-stranded DNA." Biochimica et Biophysica Acta, 1251: 125-138 (1995).

Ostermeier, Marc, et al., "A combinatorial approach to hybrid enzymes independent of DNA homology." Nature Biotechnology, 17: 1205-1209 (1999).

Parmley, Stephen F. and George P. Smith, "Antibody-selectable filamentous fd phage vectors: affinity purification of target genes." Gene, 73: 305-318 (1988).

Schier, Robert, et al., "Isolation of Picomolar Affinity Anti-c-erbB-2 Single-chain Fv by Molecular Evolution of the Complementarity Determining Regions in the Center of the Antibody Binding Site." J. Mol. Biol., 263: 551-567 (1996).

Schmidt, E. R., "Exonuclease digestion of chromosomes for in situ hybridization." Nucleic Acids Res., 16(21): 10381 (1988).

Sock, Elisabeth, et al., "DNA Replication of Human Polyomavirus JC is Stimulated by NF-I *in Vivo*." Virology, 182: 298-308 (1991).

Stemmer, Willem P. C., "Rapid evolution of a protein In Vitro by DNA shuffling." Nature, 370: 389-391 (1994).

Stemmer, Willem P. C., "DNA shuffling by random fragmentation and reassembly: In Vitro recombination for molecular evolution." Proc. Natl. Acad. Sci., 91: 10747-10751 (1994).

Vaish, Narendra K., et al., "In vitro selection of a purine nucleotide-specific hammerhead-like ribozyme." Proc. Natl. Acad. Sci., 95: 2158-2162 (1998).

Warren, Mark S., et al., "A Rapid Screen of Active Site Mutants in Glycinamide Ribonucleotide Transformylase." Biochemistry, 35: 8855-8862 (1996).

Yang, Wei-Ping, et al., "CDR Walking Mutagenesis for the Affinity Maturation of a Potent Human Anti-HIV-1 Antibody into the Picomolar Range." J. Mol. Biol., 254: 392-403 (1995).

Zhang, Ji-Hu, et al., "Directed evolution of a fucosidase from a galactosidase by DNA shuffling and screening." Proc. Natl. Acad. Sci., 94: 4504-4509 (1997).

Paabo, Svante, "Amplifying Ancient DNA." (Chapter 20) in PCR Protocols: A Guide to Methods and Applications. Academic Press, Inc. (1990).

Frank, Ronald, et al., "Simultaneous Synthesis and Biological Applications of DNA Fragments: An Efficient and Complete Methodology." Methods in Enzymology, 154: 221-249 (1987).

Deng, Su-jun, et al., "Simultaneous randomization of antibody CDRs by a synthetic ligase chain reaction strategy." Nucleic Acids Research, vol. 21, No. 18: 4418-4419 (1993).

Meyerhans, Andreas, et al., "DNA recombination during PCR." Nucleic Acids Research, 18(7): 1687-1691 (1990).

Yolov, A. A. and Z. A. Shabarova, "Constructing DNA by polymerase recombination." Nucleic Acids Research, vol. 18, No. 3: 3983-3986 (1990).

Klug, Jorg, et al., "Creating chimeric molecules by PCR directed homologous DNA recombination." Nucleic Acids Research, vol. 19, No. 10: 2793 (1991).

Saiki, Randall K., et al., "Primer-Directed Enzymatic Amplification of DNA with a Thermostable DNA Polymerase." Science, 239: 487-491 (1988).

Daugherty, Bruce L., et al., "Polymerase chain reaction facilities the cloning, CDR-grafting, and rapid expression of a murine monoclonal antibody directed against the CD18 component of leukocyte integrins." Nucleic Acids Research, vol. 19, No. 9: 2471-2476 (1991).

Krishnan, B. Rajendra, et al., "Direct and crossover PCR amplification to facilitate Tn5supF-based sequencing of λ phage clones." Nucleic Acids Research, vol. 19, No. 22: 6177-6182 (1991).

Majumder, Kamud, "Ligation-free gene synthesis by PCR: synthesis and mutagenesis at multiple loci of a chimeric gene encoding OmpA signal peptide and hirudin." Gene, 110: 89-94 (1992).

Heda, Ghanshyam D., et al., "A simple in vitro site directed mutagenesis of concatamerized cDNA by inverse polymerase chain reaction." Nucleic Acids Research, vol. 20, No. 19: 5241-5242 (1992).

Osuna, Joel, et al., "Combinatorial mutagenesis of three major groove-contacting residues of EcoRI: single and double amino acid replacements retaining methyltransferase-sensitive activities." Gene, 106: 7-12 (1991).

Jones, Douglas H. and Stanley C. Winistorfer, "Recombinant Circle PCR and Recombination PCR for Site-Specific Mutagenesis Without PCR Product Purification." BioTechniques, vol. 12, No. 4: 528-534 (1992).

Osuna, Joel, et al., "Microbial Systems and Directed Evolution of Protein Activities." Critical Reviews in Microbiology, 20(2): 107-116 (1994).

Shuldiner, Alan R., et al., "Hybrid DNA artifact from PCR of closely related target sequences." Nucleic Acids Research, vol. 17, No. 11: 4409 (1989).

Gram, Hermann, et al., "In vitro selection and affinity maturation of antibodies from a naive combinatorial immunoglobulin library." Proc. Natl. Acad. Sci., 89: 3576-3580 (1992).

Paabo, Svante, et al., "Ancient DNA and the Polymerase Chain Reaction." The Journal of Biological Chemistry, 264(17): 9709-9712 (1989).

Jansen, Ruud and Fred D. Ledley, "Disruption of phase during PCR amplification and cloning of heterozygous target sequences." Nucleic Acids Research, 18(17): 5153-5156 (1990).

Paabo, Svante, et al., "DNA Damage Promotes Jumping between Templates during Enzymatic Amplification." The Journal of Biological Chemistry, 265(8): 4718-4721.

Lewis, Alan P. and J. Scott Crowe, "Immunoglobin complementarity-determining region grafting by recombinant polymerase chain reaction to generate humanised monoclonal antibodies." Gene, 101: 297-302 (1991).

Goloubinoff, Pierre, et al., "Evolution of maize inferred from sequence diversity of an Adh2 gene segment from archaeological specimens." Proc. Natl. Acad. Sci., 90: 1997-2001 (1993).

Vallette, Francois, et al., "Construction of mutant and chimeric genes using the polymerase chain reaction." Nucleic Acids Research, 17(2): 723-733 (1988).

Sarkar, Gobinda and Steve S. Sommer, "The 'Megaprimer' Method of Site-Directed Mutagenesis." BioTechniques, 8(4): 404-407 (1990).

Higuchi, Russell, et al., "A general method of in vitro preparation and specific mutagenesis of DNA fragments: study of protein and DNA interactions." Nucleic Acids Research, 16: 7351-7367 (1988).

Innis, Michael A., et al., "PCR Protocols a Guide to Methods and Applications." Academic Press, Inc. (1990).

Higuchi, Russell, "Recombinant PCR." (Chapter 22) in PCR Protocols: A Guide to Methods and Applications. Academic Press, Inc. (1990).

Frohman, Michael A. and Gail R. Martin, "Detection of Homologous Recombinants." (Chapter 28) in PCR Protocols: A Guide to Methods and Applications. Academic Press, Inc. (1990).

Marks, James D., et al., "By-passing Immunization: Human Antibodies from V-gene Libraries Displayed on Phage." J. Mol. Biol., 222: 581-597 (1991).

Nassal, Michael and Andrea Rieger, "PCR-based site-directed mutagenesis using primers with mismatched 3'-ends." Nucleic Acids Research, 18(10): 3077-3078 (1990).

Landt, Olfert, et al., "A general method for rapid site-directed mutagenesis using the polymerase chain reaction." Gene, 96: 125-128 (1990).

Berger, Shelby L., et al., "Phoenix Mutagenesis: One-Step Reassembly of Multiply Cleaved Plasmids with Mixtures of Mutant and Wild-Type Fragments." Analytical Biochemistry, 214: 571-579 (1993).

Yon, Jeff and Mike Fried, "Precise gene fusion by PCR." Nucleic Acids Research, 17(12): 4895 (1989).

Horton, Robert M., et al., "Gene Splicing by Overlap Extension: Tailor-Made Genes Using the Polymerase Chain Reaction." BioTechniques, 8(5): 528-535 (1990).

Horton, Robert M., et al., "Gene Splicing by Overlap Extension." Methods in Enzymology, 217: 270-279 (1993).

Smith, Kelly D., et al., "Unwanted Mutations in PCR Mutagenesis: Avoiding the Predictable." PCR Methods and Applications, 2: 253-257 (1993).

Brakenhoff, Ruud H., et al., "Chimeric cDNA clones: a novel PCR artifact." Nucleic Acids Research, 19(8): 1949 (1991).

Horton, Robert M., et al., "Engineering hybrid genes without the use of restriction enzymes: gene splicing by overlap extension." Gene, 77: 61-68 (1989).

Marton, Attila, et al., "DNA nicking favors PCR recombination." Nucleic Acids Research, 19(9): 2423-2426 (1991).

Ho, Steffan N., et al., "Site-directed mutagenesis by overlap extension using the polymerase chain reaction." Gene, 77: 51-59 (1989).

Alber, et al., "Contributions of hydrogen bonds of Thr 157 to the thermodynamic stability of phage T4 lysozyme", Nature 330: 41-46 (1987).

Arrizubieta, et al., "Increased Thermal Resistance and Modification of the Catalytic Properties of a β-Glucosidase by Random Mutagenesis and in Vitro Recombination", J. Biol. Chem., 275: 28843-8 (2000).

Barbas, et al., "Assembly of combinatorial antibody libraries on phage surfaces: The gene III site", Proc. Natl. Acad. Sci. USA, 88: 7978-7982 (1991).

Barbas, et al., "Semisynthetic combinatorial antibody libraries: A chemical solution to the diversity problem", Proc. Natl. Acad. Sci. USA, 89: 4457-4461 (1992).

Berger, et al., "Expanding the Potential of Restriction Endonucleases: Use of Hapaxoterministic Enzymes", Anal. Biochem. 222:1-8, (1994).

Boder & Wittrup, "Yeast surface display for screening combinatorial polypeptide libraries", Nature Biotechnol., 15: 553-557, (1997).

Boublik, et al., "Eukaryotic Virus Display: Engineering the Major Surface Glycoprotein of the *Autographa californica* Nuclear Polyhedrosis Virus (AcNPV) for the Presentation of Foreign Proteins on the Virus Surface", Biotechnol., 13: 1079-1084, (1995).

Brown, "Chapter 5: DNA and RNA Modifying Enzymes", Molecular Biology LabFax, BIOS Scientific Publishers Ltd., Oxford, pp. 154 (1991).

Buchholz, et al., "In vivo selection of protease cleavage sites from retrovirus display libraries", Nature Biotechnol. 16: 951-954, (1998).

Cadwell, et al., "Randomization of Genes by PCR Mutagenesis", PCT Methods Appl., 2:28-33, (1992).

Cadwell, et al., "Mutagenic PCR", PCT Methods Appl., 3:S136-140, (1994).

Casson & Manser, "Evaluationof Loss and Change of Specificity Resulting from Random Mutagenesis of an Antibody $V_H$ Region", J. Immunol. 155: 5647-5654 (1995).

Chalfie, et al., "Green Florescent Protein as a Marker for Gene Expression", Science 263: 802-805 (1994).

Chang, et al., "Evolution of a cytokine using DNA family shuffling", Nature Biotech., 17: 793-797 (1999).

Chen, et al., "Tuning the activity of an enzyme for unusual environments: Sequential random mutagenesis of subtilisin E for catalysis in dimethylformamide", Proc. Natl. Acad. Sci. USA 90: 5618-5622 (1993).

Christians, et al., "Directed evolution of tymidine kinase for AZT phosphorylation using DNA family shuffling", Nature Biotech., 17: 259-264 (1999).

Crameri, et al., "Combinatorial Multiple Cassette Mutagenesis Creates All the Permutations of Mutant and Wild-Type Sequences", Biotechniques, 18: 194-196 (1995).

Crameri, et al., "Molecular evolution of an arsenate detoxification pathway by DNA shuffling", Nature Biotechnology, 15: 436-438, (1999).

Crameri, et al., "DNA shuffling of a family of genes from diverse species accelerates directed evolution", Nature, 391: 288-291 (1998).

Deng, et al., "Simultaneous randomization of antibody CDRs by a synthetic ligase chain reaction strategy", Nucl. Acid Res. 21: 4418-4419, (1993).

Dower, et al., "High efficiency transformation of E. coli by high voltage electroporation", Nucleic Acids Res. 16: 6127, (1988).

Eckstein, "Exogenous application of ribozymes for inhibiting gene expression", Ciba Found. Symp. 209: 207-217 (1997).

Engberg, et al., "Phage-Display Libraries of Murine and Human Antibody Fab Fragments", Molecular Biotechnolgoy 6: 287-310, (1996).

Ernst, et al., "Baculovirus surface display: construction and screening of a eukaryotic epitope library", Nucleic Acids Res. 26: 1718-1723, (1998).

Fisch, et al., "A strategy of exon shuffling for making large peptide repertoires displayed on filamentous bacteriophage", Proc. Natl. Acad. Sci. USA 93: 7761-7766 (1996).

Giver, et al, "Directed evolution of a thermostable esterase", Proc. Natl. Acad. Sci. USA 95: 12809-12813, (1998).

Gram, et al., "In vitro selection and affinity maturation of antibodies from a naive combinatorial immunoglobulin library", Proc. Natl. Acad. Sci. USA 89: 3576-3580, (1992).

Grabherr, et al., "Expression of Foreign Proteins on the Surface of *Autographa californica* Nuclear Polyhedrosis Virus", Biotechniques 22: 730-735, (1997).

Granzerio, et al., "Baculovirus cDNA libraries for expression of cloning genes encoding cell-surface antigens", J. Immunol. Metho. 203: 131-139, (1997).

Griffiths, et al., "Isolation of high affinity human antibodies directly from large synthetic repertoires", EMBO J., 13: 3245-3260, (1994).

Hanahan, "Studies on Transformation of *Escherichia coli* with Plasmids", Mol. Biol. 166: 557-580, (1983).

Hansson, et al., "Evolution of Differential Substrate Specificities in Mu Class Glutathione Transferases Probed by DNA Shuffling", J. Mol. Biol. 287: 265-276, (1999).

Henke & Bornscheuer, "Directed Evolution of an Esterase from Pseudomonas fluorescens. Random Mutagenesis by Error-Prone PCR or a Mutator Strain and Identification of Mutants Showing Enhanced Enantioselectivity by a Resorufin-Based Fluorescence Assay", Biol. Chem., 380: 1029-1033, (1999).

Higuchi, et al., "Cell display library for gene cloning of variable regions of human antibodies to hepatitis B surface antigen", J. Immunol. Meth., 202:193-204, (1997).

Ho, et al., "Site-directed mutagenesis by overlap extension using the polymerase chain reaction", Gene 77: 51-59, (1989).

Hoogenboom, et al., "By-passing Immunisation: Human Antibodies from Synthetic Repertoires of Germline $V_H$ Gene Segments Rearranged in Vitro", J. Mol. Biol. 227: 381-388, (1992).

Horton, et al., "Engineering hybrid genes without the use of restriction enzymes: gene splicing by overlap extension", Gene, 77: 61-68, (1989).

Huse, et al., "Generation of a Large Combinatorial Library of the Immunoglobulin Repertoire in Phage Lambda", Science, 246: 1275-1281, (1989).

Jansen, et al., "Disruption of phase during PCR amplification and cloning of heterozygous target sequences", NAR, 18: 5153-5156, (1990).

Kikuchi, et al., "Novel family shuffling methods for the in vitro evolution of enzymes", Gene 236: 159-167, (1999).

Kikuchi, et al., "An effective family shuffling method using single-stranded DNA", Gene 243: 133-137, (2000).

Kim, et al., "Bacterial Cell Surface Display of an Enzyme Library for Selective Screening of Improved Cellulase Variants", Appl. Environ. Microbiol., 66: 788-93, (2000).

Kobayashi, et al., "Analysis of Assembly of Synthetic Antibody Fragments: Expression of Functional scFv with Predefined Specificity", Biotechniques, 23: 500-503, (1997).

Kuipers, et al., "Improved site-directed mutagenesis method using PCR", Nucleic Acids Res. 19: 4558, (1991).

Kwekkeboom, et al., "CD40 plays an essential role in the activation of human B cells by murine EL4B5 cells", Immunol. 79: 439-444, (1993).

Larrick, et al., "Rapid cloning of rearranged immunoglobulin genes from human hybridoma cells using mixed primers and the polymerase chain reaction", Biochem. Biophys. Res. Commun. 160: 1250-1256, (1989).

Leung, et al., "A method for random mutagenesis of a defined DNA segment using a modified polymerase chain reaction", Technique 1:11-15, (1989).

Lewin, "Genes IV", p. 272, Oxford University Press, (1990).

Lewis & Crowe, "Immunoglobulin complementary-determining region grafting by recombinant polymerase chain reaction to generate humanised monoclonal antibodies", Gene 101: 297-302 (1991).

Liu, et al., "Replacement and deletion mutations in the catalytic domain and belt region of *Aspergillus awamori* glucoamylase to enhance thermostability", Protein Eng. 13: 655-659 (2000).

Lu & Gray, "Kinetics and mechanism of BAL 31 nuclease action on small substrates and single-stranded DNA", Biochimica et Biophysica Acta, 1251: 125-138, (1995).

Luqmani & Lymboura, "Subtraction Hybridization Cloning of RNA Amplified From Different Cell Populations Microdissected From Cryostat Tissue Sections", Anal. Biochem., 222: 102-109, (1994).

Marks, et al., "By-passing immunization: building high affinity human antibodies by chain shuffling", Biotechnology, 10: 779-783, (1992).

May, et al., "Inverting enantioselectivity by directed evolution of hydantoinase for improved production of L-methionine", Nat. Biotechnol. 18: 317-320, (2000).

McCafferty, et al., "Phage antibodies: filamentous phage displaying antibody variable domains", Nature, 348: 552-554 (1990).

Meyerhans, et al., "DNA recombination during PCR", Nucl. Acid Res., 18: 1687-91, (1990).

Moore, et al., "Directed evolution of a para-nitrobenzyl esterase for aqueous-organic solvents", Nature Biotechnology, 14: 458-467 (1996).

Mottershead, et al., "Baculoviral Display of the Green Fluorescent Protein and Rubella Virus Envelope Proteins", Biochem. Biophys. Res. Com. 238: 717-722, (1997).

Orlandi, et al., "Cloning immunoglobulin variable domains for expression by the polymerase chain reaction", Proc. Natl. Acad. Sci. USA, 86: 3833-3837 (1989).

Ostermeier, et al., "A combinatorial approach to hybrid enzymes independent of DNA homology", Nature Biotech., 17: 1205-9, (1999).

Paabo, et al., "Ancient DNA and the Polymerase Chain Reaction", J. Biol. Chem., 264: 9709-9712, (1989).

Paabo, et al., "DNA Damage Promotes Jumping between Templates during Enzymatic Amplification", J. Biol. Chem., 265: 4718-4721, (1990).

Parmely, et al., "Anitbody-selectable filamentous fd phage vectors: affinity purification of target genes", Gene 73: 305-318, (1988).

Prickett, et al., "A Calcium-Dependent Antibody for Identification and Purification of Recombinant Proteins", BioTechniques, 7: 580-589, (1989).

Roberts, et al., "Generation of an antibody with enhanced affinity and specificity for its antigen by protein engineering", Nature, 328: 731-734, (1987).

Schier R., et al., "Isolation of Picomolar Affinity Anti-c-erbB-2 Single-chain Fv by Molecular Evolution of the Complementarity Determining Regions in the Center of the Antibody Binding Site", J. Mol. Biol. 263: 551-567, (1996).

Schmidt, et al., "Exonuclease digestion of chromosomes for in situ hybridization", Nucl. Acid Research, 16: 10381, (1988).

Schmidt-Dannert, et al., "Molecular breeding of carotenoid biosynthetic pathways", Nat. Biotechnol., 18: 750-753, (2000).

Shyur, et al., "Site-directed Mutagenesis of Residues at Subunit Interfaces of Procine Fructose-1,6-bisphosphatase", J. Biol. Chem., 271: 3005-3010, (1996).

Sock, et al., "DNA Replication of Human Polyomavirus JC Is Stimulated by NF-I in Vivo", Virology, 182: 298-308, (1991).

Söderlind, et al., "Domain libraries: Synthetic diversity for de novo design of antibody V-regions", Gene, 160: 269-272, (1995).

Song, et al., "Simultaneous Enhancement of Thermostability and Catalytic Activity of Phospholipase $A_1$ by Evolutionary Molecular Engineering", Appl. Environ. Microbiol. 66: 890-894, (2000).

Stemmer, "DNA shuffling by random fragmentation and reassembly: in vitro recombination for molecular evolution", Proc. Natl. Acad. Sci. USA, 91: 10747-51, (1994).

Stemmer, "Rapid evolution of a protein in vitro by DNA shuffling", Nature, 370: 389-391, (1994).

Vaish, et al., "In vitro selection of a purine nucleotide-specific hammerhead-like ribozyme", Proc. Natl. Acad. Sci. USA, 95: 2158-2162 (1998).

Volkov, et al., "Methods for in Vitro DNA Recombination and Random Chimeragenesis", Methods Enzymol., 328: 447-456 (2000).

Wan, et al., "In vitro evolution of horse heart myoglobin to increase peroxidase activity", Proc. Natl. Acad. Sci. USA, 95: 12825-12831 (1998).

Warren, et al., "A Rapid Screen of Active Site Mutants in Glycinamide Ribonulceotide Transformylase", Biochemistry, 35: 8855-8862 (1996).

Yang, et al., "CDR Walking Mutagenesis for the Affinity Maturation of a Potent Human Anti-HIV-1 Antibody into the Picomolar Range", J. Mol. Biol., 254: 392-403 (1995).

Zhang, et al., "Directed evolution of a fucosidase from a galactosidase by DNA shuffling and screening", Proc. Natl. Acad. Sci. USA, 94: 4504-4509, (1997).

Zhao & Arnold, "Directed evolution converts subtilisin E into a functional equivalent of thermitase", Protein Eng., 12: 47-53, (1999).

Zhao, et al., "Molecular evolution by staggered extension process (StEP) in vitro recombination", Nat. Biotechnol. 16: 258-261 (1998).

Arnold FH, "Combinatorial and computational challenges for biocatalyst design", Nature (2001) 409:253-257.

Balint RF et al., "Antibody engineering by parsimonious mutagenesis", Gene (1993) 137(1):109-118.

Beaudry AA et al., "Directed evolution of an RNA enzyme", Science (1992) 257:635-641.

Berger SL et al., "Phoenix Mutagenesis: One-Step Reassembly of Multiply Cleaved Plasmids with Mixtures of Mutant and Wild-Type Fragments", Analytical Biochemistry (1993) 214:571-579.

Berkhout B et al., "In vivo selection of randomly mutated retroviral genomes", Nucleic Acids Research (1993) 21(22):5020-5023.

Blakely WF et al., "Radiation-induced binding of DNA from irradiated mammalian cells to hydroxyapatite columns", Radiant Research (1990) 121(3):338-343.

Bourgaux P et a., "Preferred crossover sites on polyomavirus DNA", Journal of Virology (1990) 64(5):2327-2336.

Casorati G et al., "The T cell receptor alpha beta V-J shuffling shows lack of autonomy between the combining site and the constant domain of the receptor chains", Eur. J. Immuno (1993) 23:586-589.

Chambers Dictionary of Science and Technology (1999), p. 995.

Clackson T et al., "Making antibody fragments using phage display libraries", Nature (1991) 352:624-628.

Crameri A, "Improved green fluorescent protein by molecular evolution using DNA shuffling", Nature Biotechnology (1996) 14:315-319.

Daugherty B et al., "Polymerase chain reaction facilitates the cloning, CDR-grafting, and rapid expression of a murine monoclonal antibody directed against the CD18 component of leukocyte integrins", Nucleic Acids Research (1991) 19(9):2471-2476.

Demple B et al., "5,6-Saturated thymine lesions in DNA: production by ultraviolet light or hydrogen peroxide", Nucleic Acids Research (1982) 10(12):3781-3789.

Dillon PJ et al., "A rapid method for the construction of synthetic genes using the polymerase chain reaction", BioTechniques (1990), 9(3):298-300.

Dimmock NJ et al., "Introduction to Modern Virology", $3^{rd}$ Ed., Blackwell Scientific Publications, 1987.

Feinberg AP et al., "A technique for radiolabeling DNA restriction endonuclease fragments, to high specific activity", Analytical Biochemistry (1983) 132:6-13.

Frappier D et al., "Alternative Homologous and Nonhomologous Products arising from Intramolecular Recombination", journal of Virology (1990) 64(10):5058-5065.

Perlak FJ, "Single step large scale site-directed in vitro mutagenesis using multiple oligonucleotides", Nucleic Acids Research (1990) 18(24):7457-7458.

Hall BG, "toward an understanding of evolutionary potential", FEMS Microbiology Letter (1999) 178:1-6.

Horton RM et al. "Gene splicing by overlap extension: tailor-made genes using the polymerase chain reaction", BioTechniques (1990) 8(5):528-535.

Horton RM et al., "Gene splicing by overlap extension", Methods Enzymol (1993) 217:270-279.

Judo MSB et al. "Stimulation and suppression of PCR-mediated recombination", Nucleic Acids Research (1998) 26(7):1819-1825.

Kauffman S et al., "Thinking combinatorially", Current Opinion in Chemical Biology (1999) 3:256-259.

Kaushansky K et al., "Structure-function relationships of interleukin-3. An analysis based on the function and binding characteristics of a series of interspecies chimera of gibbon and murine interleukin-3", J Clin Invest. (1992) 90(5):1879-1888.

Krishnan BR et al., "Direct and crossover PCR amplification to facilitate Tn5supF-based sequencing of λ phage clones", Nucleic acids Research (1991) 19(22):6177-6182.

Lassner M et al., "Directed molecular evolution in plant improvement", Current Opinion in Plant Biology (2001) 4:152-156.

Life: The Science of Biology, $3^{rd}$ Ed. (1992), Sinauer Associates, p. 55.

Lewin B, "Genes III" (1987), p. 722.

Lewin B, "Genes V" (1994), p. 647.

Lowe G et al., "Oligoneric and biogenetic combinatorial libraries", Nat. Prod. Rep. (1999) 16:641-651.

Marks JF et al., "By-passing immunization human antibodies from V-gene libraries displayed in phage", J. Mol. Biol. (1991) 222:581-597.

Marton A et al., "DNA nicking favors PCR recombination", Nucleic Acids Research (1991) 19(9):2423-2426.

Mello Filho AC et al. "In vivo formation fo single-strand breaks in DNA by hydrogen peroxide is mediated by the haber-weiss reaction", Biochim. Biophys. Acta (1984) 781:56-63.

Merz A et al., "Improving the catalytic activity of a thermophilic enzyme at low temperatures", Biochemistry (2000) 39:880-889.

Molecular Cell Biology, $3^{rd}$ Ed., (1995), W.H. Freeman and Company, p. G-16.

Mouret JF et al., "Ionic and radiacal oxidations of DNA by Hydrogen Peroxide", Chem. Biol. Interact. (1991) 77(2):187-201.

Mullis K et al., "Specific Enzymatic Amplification of DNA In Vitro: the Polymerase Chain Reaction", Spring harbor Symp., Quant. Biol. (1986) 51:263-273.

NCBI database entries (partial) for *Homo sapiens* insulin, myoglobin, L-selectin, rhodopsin kinase and complement component C3 mRNAs.

Near RI, "Gene Conversion of Immunoglobulin Variable Regions in Mutagenesis Cassettes by Replacement PCR Mutagenesis", Biotechniques (1992) 12(1):88-97.

Ness JE et al., "DNA shuffling of subgenomic sequences of subtilisin", Nature Biotechnology (1999) 17:893-896.

Ness JE et al., "Molecular Breeding: the natural approach to protein design", Advances in Protein Chemistry (2001) 55:261-292.

Ørum H et al., "Efficient method for constructing comprehensive murine Fab antibody libraries displayed on phage", Nucleic Acids Research (1993) 21(19):4491-4498.

Patten AP et al., "Applications of DNA shuffling to pharmaceuticals and vaccines", Current Opinion in Biotechnology (1997) 8:724-733.

Perlak FJ, "Single step large scale site-directed in vitro mutagenesis using multiple oligonucleotides", Nucleic Acids Research (199) 18(24):7457-7458.

Povirk LF et al., "Oxidized apurinic/apyrimidinic sites formed in DNA by oxidative mutagens", Mutation Research (1989) 214:13-22.

Powell SK et al., "Breeding of retroviruses by DNA shuffling for improved stability and processing yields", Nature Biotechnology (2000) 18:1279-1282.

Prodromou C et al., "Recursive PCR: a novel technique for total gene synthesis", Protein Engineering (1992) 5:827-829.

Punnonen J, "Molecular Breeding of Allergy Vaccines and Antiallergic Cytokines", International Archives of Allergy Immunology (2000) 121:173-182.

Punnonen J et al., "Molecular Breeding by DNA Shuffling", Science & Medicine (2000) 121:38-47.

Rhaese HJ et al., "Chemical analysis of DNA alterations. I. Base liberation and backbone breakage of DNA and oligodeoxyadenylic acid induced by hydrogen peroxide and hydroxylamine", Biochim. Biophys. Acta (1968) 155:476-490.

Sagripanti JL et al., "Site-specific oxidative DNA damage at polyguanosines produced by copper plus hydrogen peroxide", Journal of Biological Chemistry (1989) 264(5):1729-1734.

Saiki RK et al., "Primer-directed enzymatic amplification of DNA with a Thermostable DNA polymerase", Science (1988) 239(4839):487-491.

Sambrook J et al., "Molecular Cloning" (1989) Chapters 16-18.

Shi XB et al., "Rapid PCR construction of a gene containing Lym-1 antibody variable regions", PCR Methods and Applications (1993) 3:46-53.

Shuldiner AR et al., "Hybrid DNA artifact from PCR of closely related target sequences", Nucleic Acids Research (1989) 17(11):4409.

Soogn NW et al., "Molecular breeding of virses", Nature Genetics (2000) 25;436-439.

Suzuki DT et al., "An Introduction to Genetic Analysis", 4$^{th}$ Ed., W.H. Freeman and Company, p. 332.

Tobin MB et al., "Directed evolution: the 'rational' basis for 'irrational' design", Current Opinion in Structural Biology (2000) 10:421-427.

Weisberg EP et al., "Simultaneous mutagenesis of multiple sites: application of the ligase chain reaction using PCR products instead of oligonucleotides", Biotechniques (1993) 15(1):68-70, 72-74, 76.

Whalen RG et al., "DNA shuffling and vaccines", Current Opinions in Molecular therapeutics (2001) 3:31-36.

Zaphiropoulos PG et al., "Non-homologous revombination mediated by Thermus aquaticus DNA polymerase I. Evidence supporting a copy choice mechanism", Nucleic Acids Research (1998) 26(12):2843-2848.

Zoller MJ et al., "New recombinant DNA methodology for protein engineering", Current Opinion in biotech (1992) 3:348-354.

Horton RM et al. (1991), "Recombination and mutagenesis of DNA sequences using PCR", Directed Mutagenesis: A Practical Approach. M.J. McPherson, ed. IRL Press, Oxford, p. 217-247.

Malmborg, A-C., "Molecular libraries," website printout, 2 pages, www.immun.lth.se/texter/project mol-libraries.html (Dec. 8, 2005).

Henriquez, V., et al., "A simple strategy to generate small deletions using Bal31 nuclease," Nuc. Acids Res., 18:6735-6736, (1990).

Horton, R.M., et al., "Gene splicing by overlap extension," Methods in Enzymology, 317:270-279, (1993).

Brown, T.A., ed., Molecular Biology LabFax I: Recombinant DNA, Academic Press, San Diego, 128-129, (1998).

Ostermeier, M., et al., "Combinatorial protein engineering by incremental truncation," Proc. Natl. Acad. Sci. USA, 96:3562-3567, (1999).

Sharrocks, A., et al., "A rapid method for Bal31 deletion analysis," Nuc. Acids Res., 15:8564, (1987), (Abstract).

* cited by examiner

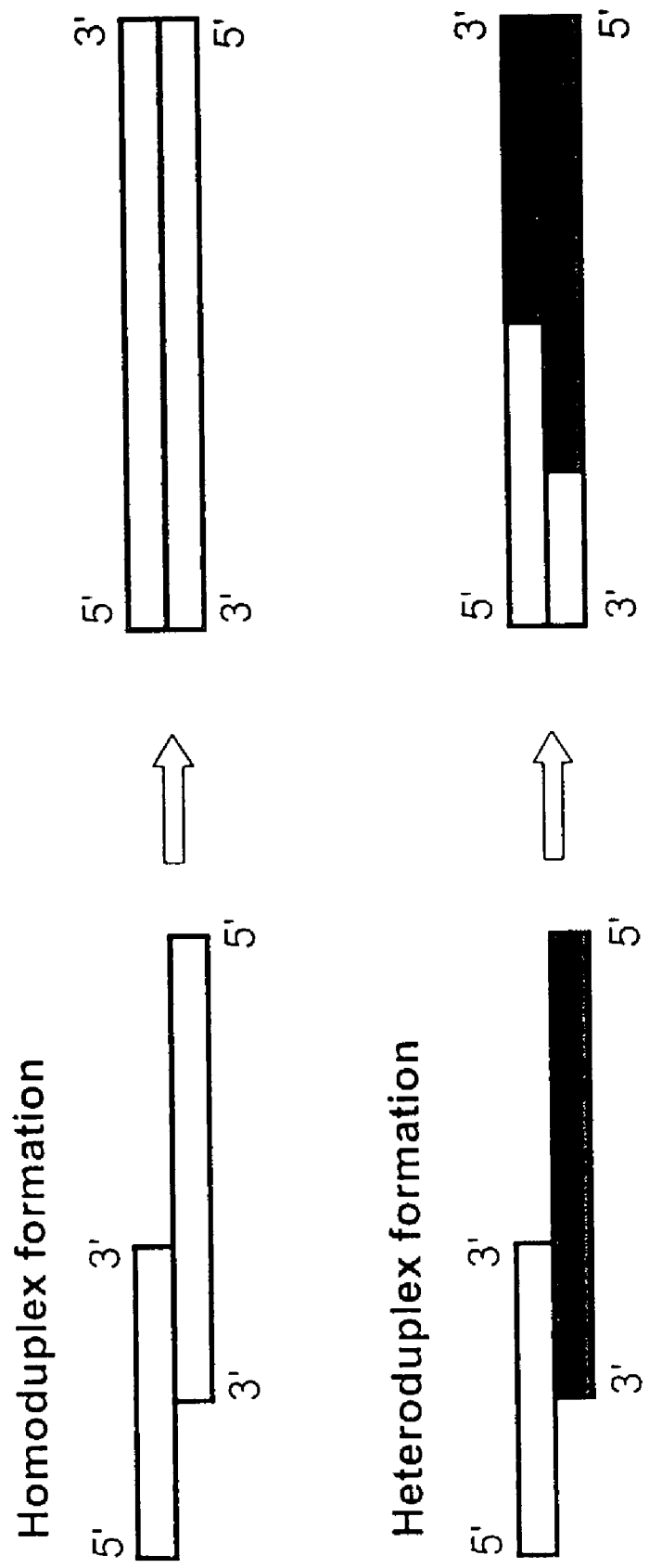

SYNTHESIS OF HYBRID POLYNUCLEOTIDE MOLECULES USING SINGLE-STRANDED POLYNUCLEOTIDE MOLECULES

This application is a continuation of U.S. patent application Ser. No. 09/742,123 filed Dec. 22, 2000, now abandoned, entitled "Synthesis of Hybrid Polynucleotide Molecules Using Single-Stranded Polynucleotide Molecules", the entire disclosure of which is incorporated by reference herein.

BACKGROUND OF THE INVENTION

1. Field of the Invention

The present invention relates to a method for the production of hybrid polynucleotide molecules from two parental polynucleotide molecules using single-stranded polynucleotides, which can achieve superior effects to the existing methods, such as a higher frequencies.

2. Description of the Related Art

DNA shuffling is a developed technique that allows accelerated and directed protein evolution in vitro. In this method, the acquisition of genes encoding improved proteins is done in two steps. In the first step, a single gene is mutagenized, and desired mutant genes are selected. In the second step, the mutant genes are fragmented by DNase I, and subsequently recombined in vitro by using PCR. Among the recombinants, (i.e., the products of DNA shuffling), those producing most favored proteins are isolated (FIG. 1; 1, 2). The modified versions of the DNA shuffling exist: (i) random priming was used to generate DNA fragment instead of the DNase I digestion (3); (ii) PCR conditions with very short annealing/extension steps were employed to increase the frequency of recombination (4). Using these techniques, a number of improved enzymes have been obtained (1-9). When the DNA shuffling is done using a set of homologous genes instead of a set of mutant genes derived from a single gene, this technique is called family shuffling. Family shuffling utilizes naturally occurring nucleotide substitutions among family genes as the driving force for the in vitro evolution. The application of the family shuffling strategy has also provided many successful examples (10-15).

A potential problem of the family shuffling is a low yield of recombinants (i.e., hybrid molecules constituted from several family gene sequences). When two parental genes of 80% nucleotide sequence identity were shuffled, the frequency of hybrid formation was less than 1% (16-17). The low recombination yield may be due to a lower frequency of the heteroduplex formation compared to the frequency of the homoduplex formation (FIG. 2; 16).

Thus, it is desirable to develop methods which allow for the high frequency production of recombinant molecules of two or more family genes. We have reported a technique which is the shuffling of restriction endonuclease-digested DNA fragments instead of the shuffling of randomly fragmented DNA (16). The annealing of endonuclease-digested DNA fragments would produce homoduplex at a high frequency, but significant DNA elongation only occurs on the heteroduplex molecules.

SUMMARY OF THE INVENTION

Contemporary genes belonging to the same gene family are derived from a single ancestral gene after repeated introduction of mutations through the natural divergent evolution processes (FIG. 3). The shuffling of the family gene sequences creates a library of chimeric genes which would yield gene products of diverse properties. Among the diverse propertied expressed from the chimeric genes, desired ones could be selected.

In the shuffling of family genes in conventional methods (1-11, 13-15, 18), two types of annealing occur: homoduplex (annealing of strands derived from the same gene) and heteroduplex (annealing of strands derived from two different genes) (FIG. 2). If the frequency of the homoduplex formation is higher than that of the heteroduplex formation, the frequency of the regeneration of the original gene sequences through PCR reactions occurs preferentially rather than the formation of chimeric genes. The consequence of it is a low yield of recombinant molecules of two or more family genes.

Now, we invented a new technique which uses single-stranded polynucleotide sequences (17). In this method, single-stranded polynucleotides of two family genes are prepared. One single-stranded polynucleotide is the coding strand of one gene while another single-stranded polynucleotides is the non-coding strand of another gene. These two single-stranded polynucleotide molecules are fragmented into appropriate sizes, and their fragments are used for the family shuffling. This technique is preferable in that, in the first round of hybridization, the homoduplex formation is prevented.

Based on this new technique, we completed the present invention which can provide hybrid polynucleotide molecules from parental polynucleotides containing one or more parts of homology and one or more parts of heterology (e.g., family genes).

In this invention, two types of single-stranded polynucleotides are prepared from two parent polynucleotids (for example, two family genes, two genes obtained by random mutagenesis of a parental gene, etc.), and used for the in vitro polynucleotide synthesis. The first type is the single-stranded polynucleotide molecule corresponding to the coding strand of, for example, one family gene while the second type is the single-stranded molecule corresponding to the non-coding strand of, for example, another family gene. In other words, these two types of the single-stranded polynucleotide molecules are complementary to each other but have one or more parts which are not complementary (the first-type molecule comprises one or more parts of homology and one or more parts of heterology to the complementary sequence of the second-type molecule). These single-stranded polynucleotide molecules are fragmented into appropriate sizes, and hybridized. In this procedure, no homoduplex molecule is formed, and when appropriate enzyme(s) exists, the nucleotide elongation can occur on heteroduplex molecules forming chimeric polynucleotide pieces. (FIG. 4) Subsequently, the steps of the denaturation followed by hybridization and polynucleotide synthesis could be done repeatedly as summarized in FIG. 1.

This method can be combined to appropriate methods for introducing one or more mutations into chimeric genes.

Thus, the present invention provides inter alia:

(1) A method for making libraries of hybrid polynucleotide molecules in which double-stranded polynucleotide molecules are not used as starting materials.

(2) The method of (1) above, wherein two types of single-stranded polynucleotide molecules are used as starting materials and wherein the first-type molecule comprises stretches of sequences containing one or more parts of homology and one or more parts of heterology to the complementary sequence of the second-type molecule.

(3) The method of (2) above, wherein the single-stranded polynucleotide molecules are fragmented and used as templates for de novo polynucleotide synthesis to create hybrid polynucleotide molecules.

(4) The method of (2), wherein mutations are introduced into hybrid polynucleotide molecules prior, during or after the production of the hybrid polynucleotide molecules.

(5) A method for making libraries of hybrid polynucleotide molecules, which comprises:

(i) preparing two single-stranded polynucleotide molecules comprising sequences which are complementary to each other, (ii) randomly or non-randomly fragmenting the two single-stranded polynucleotide molecules, (iii) incubating the fragmented molecules under conditions such that hybridization of fragmented polynucleotide molecules occurs and de novo polynucleotide synthesis on the hybridized molecules occurs, (iv) denaturing the resultant elongated double-stranded polynucleotide molecules into single-stranded polynucleotide molecules, (v) incubating the resultant single-stranded polynucleotide molecules under conditions such that hybridization of single-stranded polynucleotide molecules occurs and de novo polynucleotide synthesis on the hybridized molecules occurs, and (vi) repeating at least two further cycles of steps (iv) and (v).

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIGS. 4A and 4B illustrates hybridization of polynucleotides and nucleotide synthesis in family shuffling.

4A: Two polynucleotide strands (e.g. DNA) of two family genes are indicated by open and close boxes. In the family shuffling using two genes, two types of annealing occur: homoduplex (annealing of strands derived from the same gene) and heteroduplex (annealing of strands derived from two different genes). If the frequency of the homoduplex formation is higher than that of the heteroduplex formation, the frequency of the regeneration of the original (parental) gene sequences occurs preferentially rather than the formation of chimeric genes.

4B: To prevent the homoduplex formation in the first round of nucleotide synthesis, single-stranded polynucleotide molecules are prepared from two family genes. These single-stranded polynucleotide molecules are fragmented by appropriate methods (e.g. by DNase I digestion), and hybridized. In contrast to conventional methods using double-stranded polynucleotide molecules, only heteroduplex molecules are formed in this invention.

Figure 5:
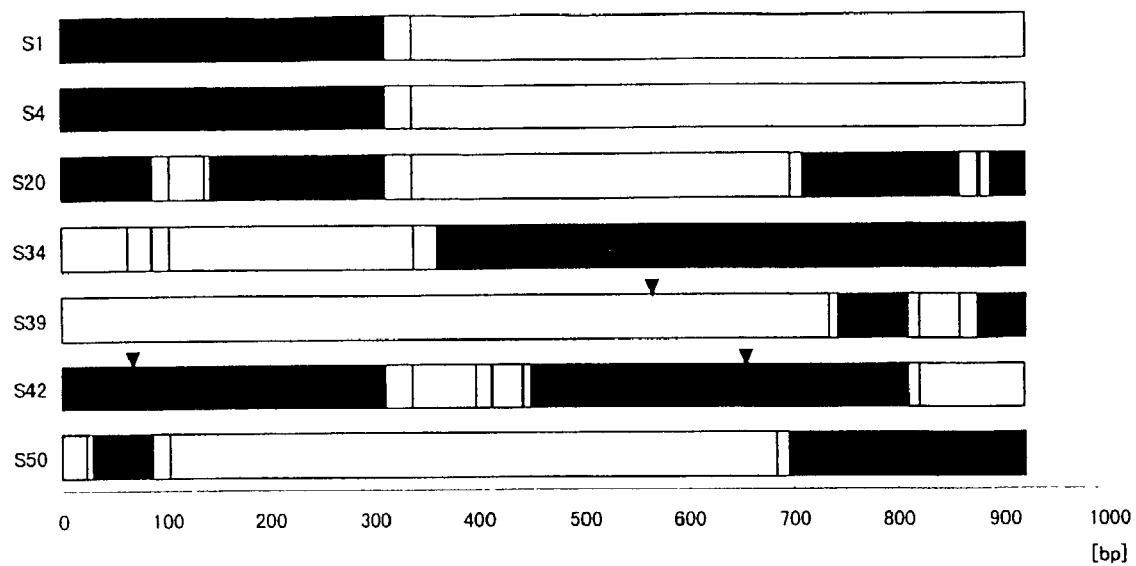

FIG. 5 illustrates chimeric structures of the single-stranded DNA-based shuffling products. This is an example where single-stranded DNAs of nahH and xylE were shuffled, fifty shuffled clones exhibiting the C23O activity were randomly selected, and their nucleotide sequences were determined as described in Example below. The sequences derived from nahH and xylE are shown by shaded and solid boxes, respectively. White boxes show the expected recombination regions, and solid triangles show the point mutations.

DETAILED DESCRIPTION OF THE INVENTION

The term "parental polynucleotide molecule" is used to indicate a polynucleotide molecule species which is a starting material for in vitro manipulations.

The term "hybrid polynucleotide molecule" is used to indicate that the polynucleotide molecule is constituted from sequences derived from several parental polynucleotide molecules. The hybrid polynucleotide molecule may or may not contain base substitution(s) comparing to the parental sequences as mutation(s) can be introduced during the processes forming the hybrid polynucleotide molecule.

The term "initial template" is used to indicate that this molecule is used as a starting material for in vitro manipulations, and served as a template for the de novo polynucleotide synthesis.

The term "complementary" is used to mean that two polynucleotide sequences is homologous (not necessarily 100% identical) enough to make a stable hybridized molecules at a temperature above 0° C.

The term "random or non-random fragmentation" means the process to generate polynucleotide molecules shorter than the length of an initial template. The fragmentation can be attained by several means, for example, by either the digestion of a single-stranded polynucleotide by appropriate nuclease(s), a physical shearing (e.g. sonication) of a polynucleotide molecule, or random priming of a polynucleotide to synthesize polynucleotide fragments complementary to the template sequence.

The term "in vitro manipulations" is used to mean various in vitro manipulations required for the synthesis of hybrid polynucleotide molecules starting from two or more types of homologous polynucleotide molecules.

The terms "homology" and "homologous" is used to indicate that the partial sequences of two or more polynucleotide molecules are either the same or similar to each other, or highly complementary to each other so that two complementary strands derived from two substantially homologous sequences can stably hybridize each other at a temperature above 0° C. The term "heterology" is used to indicate the opposite meaning.

Figure 1:
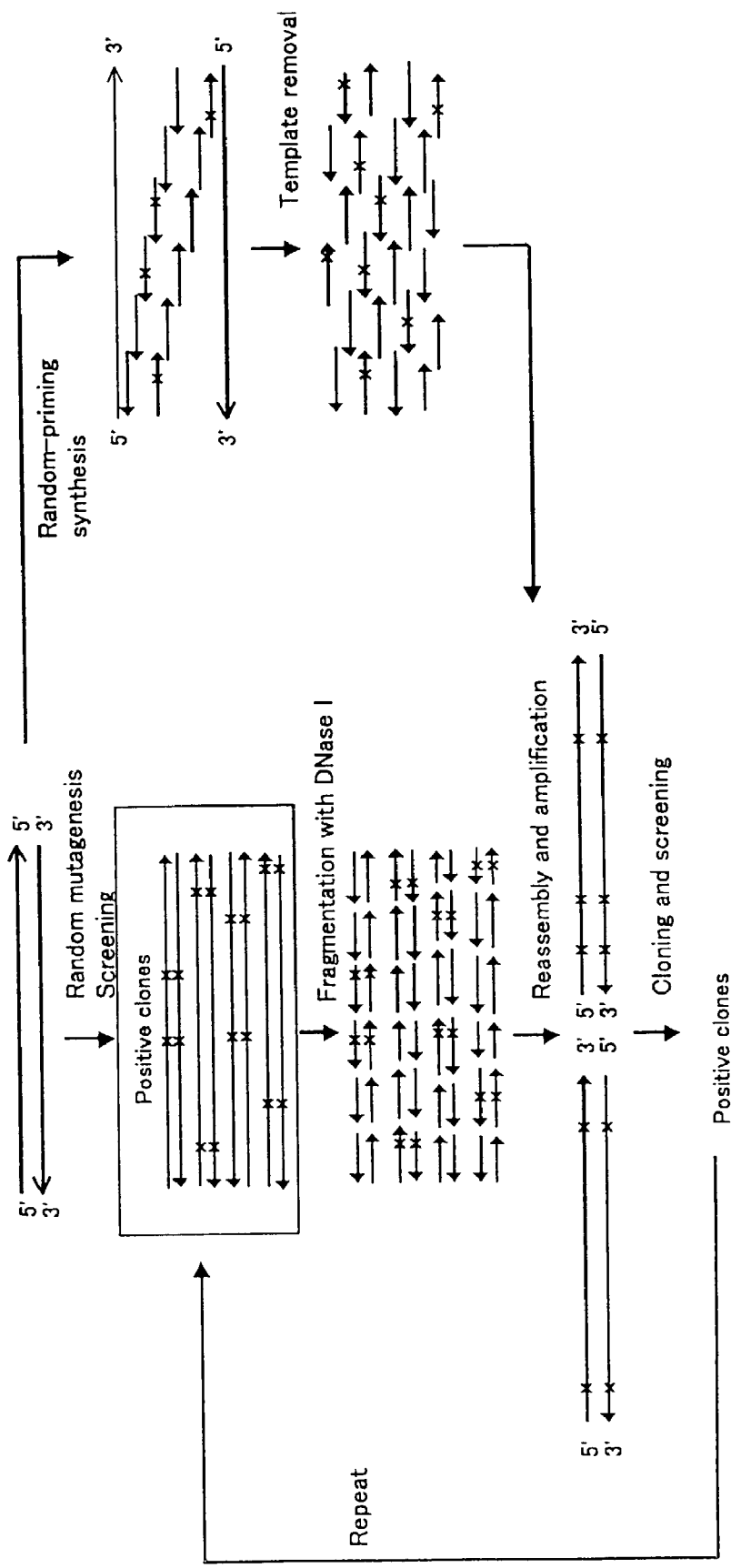
FIG. 1 illustrates a concept of DNA shuffling. The method for in vitro evolution of genes generally called DNA shuffling consists of repeated cycles of two steps: random mutagenesis and DNA shuffling of mutations. In the first step (random mutagenesis/screening), several mutants are isolated from a target gene. In the second step, the mutant genes are segmented (usually by DNase I), then reassembled by PCR without primer. The reassembled molecules are further amplified by PCR with appropriate primers. DNAs created by DNA shuffling are used to transform a recipient (usually *Escherichia coli*), and transformed strains are selected for desired phenotypes. Instead of the DNase I segmentation, random-priming synthesis of short fragments can be used.

The DNA shuffling methods (1-11, 13-15, 18) have been developed for accelerated and directed protein evolution in vitro. The methods generally consist of two steps: (i) the isolation of several improved mutants of the gene, and (ii) the in vitro recombination of the mutant genes followed by the selection of best progenies. In FIG. 1, these steps are illustrated. In the first step, a single gene is mutagenized by one of established methods, and desired mutant genes are selected. In the second step, the fragments of the mutant genes are obtained e.g. by DNase I treatment or random priming, and the mixture of the fragments is subjected to PCR without primer. DNA pieces derived from different mutants are recombined in this PCR. Next, PCR was carried out with forward and reverse primers to amplify the full-length DNA segments.

Instead to use a set of mutant derivatives as shown in FIG. 1, a set of homologous genes could be shuffled to obtain genes synthesizing improved enzymes. This technique is called family shuffling. Family shuffling utilizes naturally occurring nucleotide substitutions among family genes as the driving force for the in vitro evolution. A potential problem of the family shuffling is a low yield of recombinants (i.e., hybrid molecules constituted from several family gene sequences). When two parental genes of 80% nucleotide sequence identity (xylE and nahH, see Examples) were shuffled, the frequency of hybrid formation was less than 1% (16-17).

Thus, it is desirable to develop methods which allow for the high frequency production of recombinant molecules of two or more family genes. The present invention relates to the DNA shuffling methods summarized in FIG. 1, but is different from them in which single-stranded polynucleotide molecules are used as starting materials instead of double-stranded polynucleotide molecules. As described below, this method allowed recombination of family genes, etc. at a frequency higher than that in conventional DNA shuffling methods.

Figure 2:
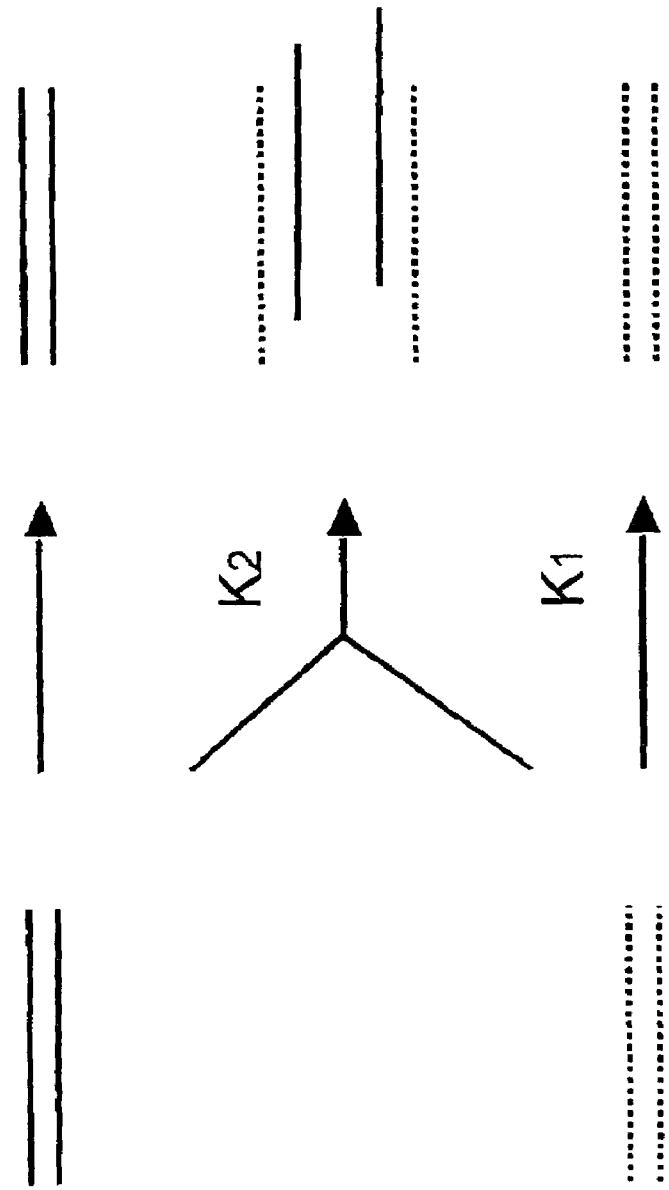
FIG. 2 illustrates formation of homoduplex and heteroduplex from two parental polynucleotide molecules whose sequences are similar. When two parental polynucleotide molecules whose sequences are similar but not identical to each other are denatured and hybridized, two types of hybridized molecules are formed: one strand of polynucleotide molecule hybridized with a complementary strand derived from the same parent (homoduplex), and that hybridized with a complementary strand derived from a different parent (heteroduplex). The velocity constant for the homoduplex formation ($k_1$) may be higher than that for the heteroduplex formation ($k_2$).
Figure 3:
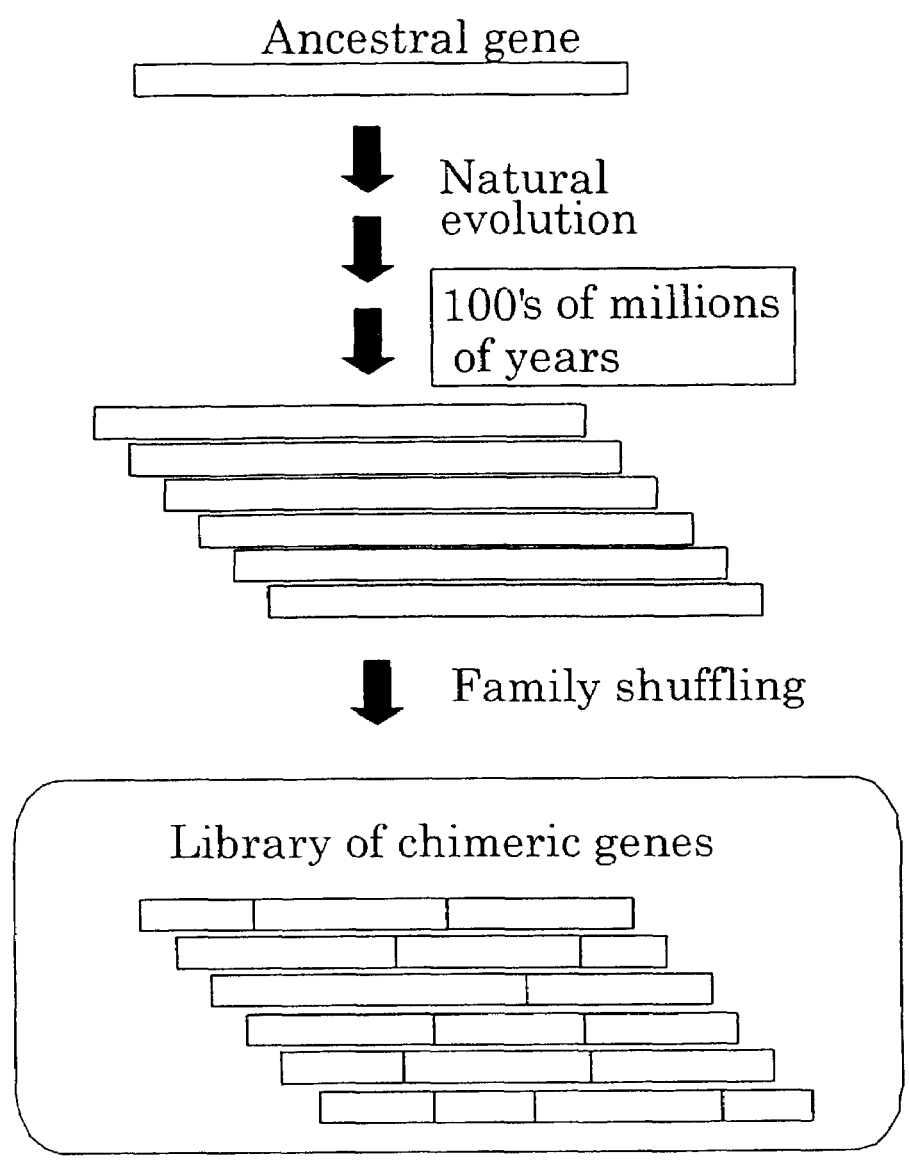
FIG. 3 illustrates a concept of family shuffling. Contemporary genes belonging to the same gene family are derived from a single ancestral gene after repeated introduction of mutations through the natural divergent evolution processes. The shuffling of the family gene sequences creates a library of chimeric genes from which desired chimera are selected.
Figure 4B:
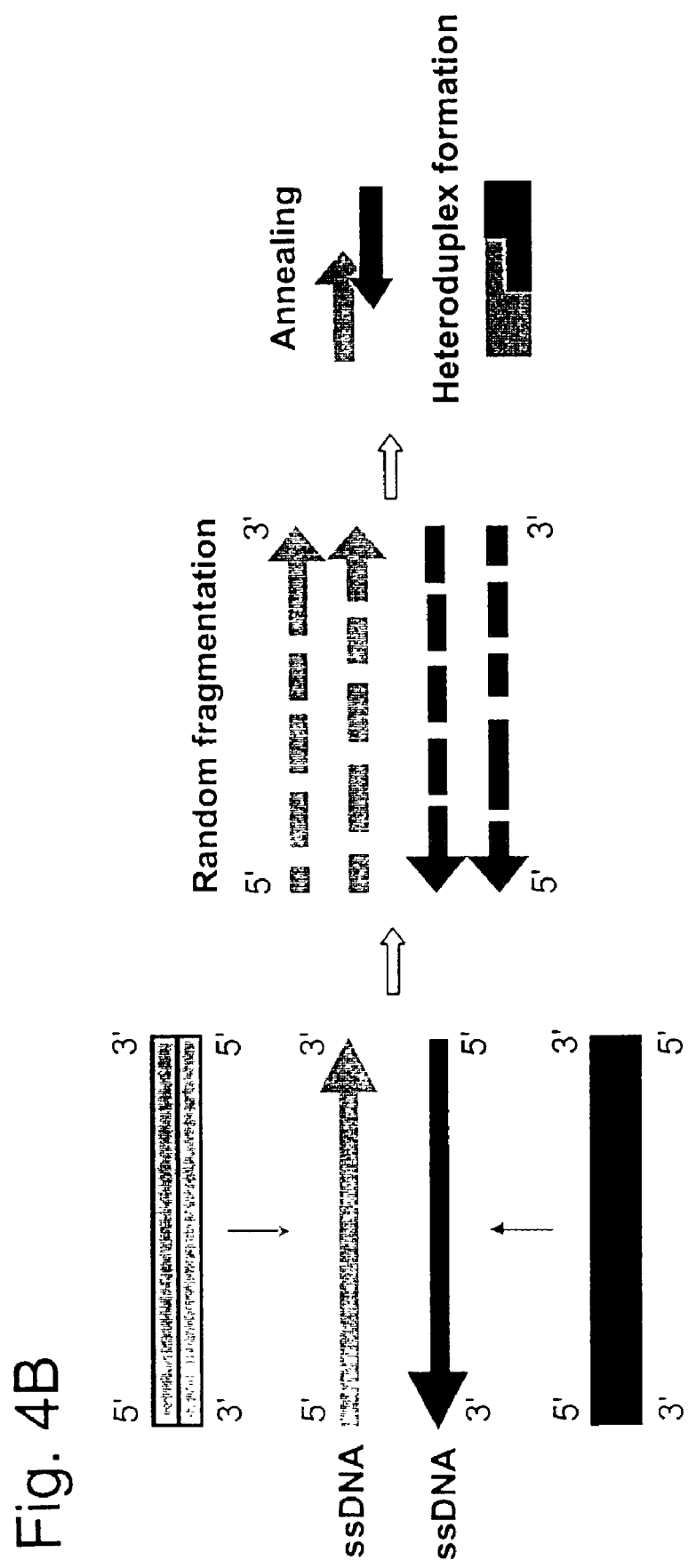

After the failure of the family shuffling in our hands, we considered possible reasons for it. For the successful generation of recombinant progeny of two family gene, A and B, the hybridization between single-stranded DNA of A and B (heteroduplex) should be formed, on which the elongation of DNA proceeds to form a recombined molecule of A and B (FIG. 4A). However, in this method, the hybridization between A and A or that between B and B also occur forming homoduplex molecules (FIG. 2). If the probability of the formation of heteroduplex molecules (a A strand hybridized with a B strand) is smaller than that of homoduplex molecules, i.e. a A (or B) strand hybridizing with another A (or B) strand (FIG. 2), the frequency of the hybrid molecules between A and B may be very low in the products of the family shuffling. A computer simulation demonstrated that this inference would be the case.

To obtain a high frequency recombination in the polynucleotide shuffling, we newly conceived to elevate the probability of the formation of heteroduplex molecules or reduce the probability of the formation of homoduplex molecules. In an attempt to increase the probability of the heteroduplex formation in the family shuffling of xylE and nahH (see below, Examples), the annealing temperature in the PCR reactions was lowered. However, the majority of the shuffling products still had a structure of either xylE or nahH (i.e., the frequency of the formation of xylE-nahH hybrids was very low).

We interpreted these results as indicating that the probability of homologous pairing is much higher than that of heterologous pairing in the shuffling of two genes of modest homology (e.g. about 80% homology). We then attempted to decrease the probability of homoduplex formation. For the successful generation of recombinant progeny of two family genes, the hybridization between a single-stranded polynucleotide molecule of one family gene and a single stranded polynucleotide molecules of another family gene is required. However, in the conventional family shuffling methods, the hybridization of two strands derived from the same gene would occur preferentially over the hybridization of two strands each of which is derived from different family genes.

As a result of extensive studies, we newly found that use of single-stranded polynucleotide for shuffling can achieve the object of the present invention.

The present invention used single-stranded polymucleotides instead of double-stranded DNA as starting materials for preparing hybrid polynucleotide molecules from the parental polynucleotides. Thus, the present invention provides a method for making libraries of hybrid polynucleotide molecules, a method for forming a mutagenized double-stranded polynucleotide, a method for obtaining a chimeric polynucleotide sequence, etc., wherein single-stranded polymucleotides instead of double-stranded DNA are used as starting materials.

One embodiment of the method of the present invention includes the following steps:

(i) preparation of two single-stranded polynucleotide molecules comprising parts of sequences which are complementary to each other, (ii) random or non-random fragmentation of them, (iii) hybridization of the fragmented molecules followed by polynucleotide synthesis (i.e. polynucleotide chain elongation) on the hybridized molecules, (iv) separation of the chain elongation products (i.e. double-stranded polynucleotide molecules) into single-stranded polynucleotide molecules (denaturation), (v) hybridization of the resultant single-stranded polynucleotide molecules followed by polynucleotide synthesis on the hybridized molecules, and (vi) repeating at least two further cycles of step (iv) and (v) (e.g., under PCR conditions).

The present invention involves in the formation of hybrid polynucleotide molecules by mixing two parental polynucleotide sequences. The partial homology should exist between two parental polynucleotide sequences so that the complementary strands derived from some regions of the two parental polynucleotide molecules can hybridize each other under conditions required for the de novo polynucleotide sequences. In other words, two complementary polynucleotide sequences have one or more parts of homology and one or more parts of heterology from each other. The required homology is dependent upon several parameters including the G-C contents of the parental molecules. The present invention is applicable even if the total homology is low, e.g., less than about 95%, and even less than about 80%. Preferably, each of the homologous regions (i.e., parts of homology) should be at least 15-base-long with the homology higher than 75%.

The total length of the two polynucleotide sequences are not particularly limited. Generally, about 30 bases to about 10,000 bases are preferable, and about 100 bases to about 2,000 bases are more preferable.

In the case where the mixing of more than two parental polynucleotide sequences is desired, hybrids of two parental sequences should be formed first, then, the single-stranded polynucleotide sequences of the hybrids should be prepared to mix with the third parental polynucleotide sequences.

Various methods existing for single-stranded DNA preparation can be utilized in the present invention. As an example of one method, the genes have to be cloned either in a phagemid vector or in a single-stranded DNA phage such as M13, and the single-stranded DNA have to be prepared from the filamentous phage particles. Two homologous genes contain regions separately cloned in phagemid vectors (for example, pBluescript) or single-stranded DNA phage vectors. The orientations of one gene with respect to the origin of the single-stranded DNA replication should be the same, while that of another gene should be opposite with respect to the origin of the single-stranded DNA replication. Then, the coding strand of one gene and the non-coding strand of another gene are synthesized and packaged in phage particles. In other words, single-stranded DNAs of the two homologous genes are complementary to each other.

The plasmids thus constructed are introduced into "male" E. coli such as JM109 (as the infection by single-stranded DNA phage requires F pili). If phagemids are used, cultures of the transformants should be infected with a helper phage such as VCS-M13 (Stratagene) or M13KO7 (Pharmacia) to rescue of single-stranded DNA from the phagemids.

In supernatant of the culture, phagemid DNA packaged in phage capsules as well as helper phage are recovered. Single-stranded DNA is then prepared from the phage capsules reactions. The presence of the helper phage DNA does not interfere with the following reactions.

Other methods than using phagemid/phage vectors exist for the preparation of single-stranded DNA: asymmetric PCR is one of such techniques.

The single-stranded DNA obtained prepared above may contain a double-stranded DNA as a contaminant, but the amount of the double-stranded DNA is preferably controlled to 30% or less, more preferably 5% or less.

The single-stranded DNA is then fragmented by an appropriate method. The degree of fragmentation (i.e., length of fragmented polynucleotides) is not particularly limited. One skilled in the art can optionally decide the degree of fragmentation taking into consideration the full length of the polynucleotides to be shuffled, the GC content thereof, the intended degree of shuffling, etc.

Examples of the method to achieve fragmentation include use of DNase I, but other methods such as shearing by sonication can also be used. In general, fragments in the size range larger than 20 bases may be isolated from 2-3% low-melting-point agarose gel. Thus, preferably, the fragmentation may be controlled so that the average length of the fragmented polynucleotides is from about 20 to about 500 bases. Our data showed that the size range of about 40-200 bases is further preferable for the mixing of two polynucleotide sequences of lower homology (e.g., about 80% homology), but the present invention is not limited to this range.

If regions with low sequence homologies exist, uninterrupted polynucleotide segments covering these heterogenous regions should be prepared as the hybridization and hence the recombination of two parental polynucleotide molecules would not occur at a high frequency in these regions.

Fragments of single-stranded DNA thus prepared are then used for the reassembly of fragments and amplification of assembled fragments, the steps commonly used by conventional DNA shuffling methods. Examples of family shuffling using single-stranded DNA were described below (see Examples). The frequency of the chimerical gene formation using single-stranded DNA was much higher than that using the original DNA shuffling methods with double-stranded DNAs.

In the single-stranded DNA-based methods using two family genes, single-stranded fragments of one gene could anneal only to single-stranded fragments of another gene at the 1st hybridization cycle. In the case that a mixture of single-stranded and double-stranded polynucleotide molecules is used for the $1^{st}$ hybridization cycle, (if single-stranded polynucleotide molecules are prepared by asymmetric PCR, the product is the mixture of the double-stranded and single-stranded polynucleotide molecules), the probability of the heteroduplex formation is not 100%, but it is higher than that using solely double-stranded polynucleotide molecules. Although the elongation products could make homoduplex at the 2nd or later cycles, the frequency of the heteroduplex formation would be higher in the shuffling using single-stranded DNA than that in the shuffling using double-stranded DNA.

When single-stranded DNA was used as a starting materials, the frequency of hybrid formation was 17% when two genes (xylE and nahH) having sequence divergence of about 20%. This frequency was lower than that of the restriction enzyme-based DNA shuffling in which almost all shuffling products were chimerical genes (16). However, although the restriction enzyme-based DNA shuffling has many advantages, the variety of shuffling products might be limited to a certain degree, because the variation of gene fragments generated by restriction enzyme digestion were limited compared to that generated by random fragmentation.

In the in vitro protein evolution, both the efficient recombination of genes and the effective screening of recombinants are required. If a very effective screening method, such as antibiotic resistance, is available, the desired chimeras would be obtained even if the recombination efficiency is low. We could cite the selection of improved β-lactamase as an example of easy screens. In this case, one variant among $10^6$ progenies could easily be selected. However, for the improvement of most industrially relevant enzymes, no selection is possible. The enzyme properties in progenies should be determined, one to the other, by using time-consuming assays. Under such circumstances, shuffling techniques with efficient recombination are of use even though these techniques require additional manipulations.

Other detailed conditions, reagents to be used, procedures, etc. for the above-described steps such as preparation of single-stranded DNA, random or non-random fragmentation of DNA molecules, annealing (hybridization), separation of double-stranded DNA into single-stranded DNA, polynucleotide synthesis (i.e., polynucleotide chain elongation) on the hybridized molecules, etc. can be appropriately decided by taking into consideration those known in the art, for example, in "Molecular Cloning, A Laboratory Manual" (edit. by T. Maniatis et al., Cold Spring Harbor Laboratory, 1989), U.S. Pat. No. 5,830,721, etc., both herein incorporated by reference.

In conclusion, the present invention provides a shuffling method using single-stranded DNA which can increase the probability of the hybrid formation comparing with that using double-stranded DNA. This technique should be especially useful for the family shuffling of any genes.

EXAMPLE

The following results are one example of many possible embodiments of the present invention.

(1) Family Shuffling of xylE and nahH Using Double-stranded DNA

The xylE and nahH genes both encode catechol 2,3-dioxygenase (C23O). Their nucleotide sequences are approximately 80% identical. When we applied the previously described family shuffling techniques to obtain hybrid genes of xylE and nahH, the formation of chimeric genes was severely restricted, and only the parental genes, nahH and xylE, were generated as described below.

According to the method outlined by Zhao et al. (18), we carried out the family shuffling between xylE and nahH, and the products of the family shuffling were cloned in pBluescript SK(+). After the transformation of *E. coli* cells using the ligated DNA, about 50% of the colonies developed on the selective plated showed the C23O activity. When 50 clones showing the C23O activity were randomly selected and their C23O genes were sequenced, it was found that none of them were chimeric. Most of the products had the structure of xylE (26 clones), nahH (15 clones), or their point mutants (9 clones). Fifty additional clones were checked, however, no single chimerical gene was found. All those results demonstrated that the frequency of hybrid formation was less than 1%.

Thus, preventing the formation of the original gene structures has become quite important for successful family shuffling between nahH and xylE.

(2) Family Shuffling Using Single-stranded DNA

Family shuffling using single-stranded DNA were performed as described in sections (3) and illustrated in FIG. 4. After the transformation of *E. coli* cells, about 64% of the colonies grown on plates showed the C23O activity. When randomly selected 50 clones exhibiting the C23O activity were analyzed for the nucleotide sequences of their C23O genes, 7 of them (14%) were chimerical, and the other were either parental genes (40 clones) or their point mutants (3 clones). The structures of the chimerical clones were shown in FIG. 5. Two of them, hybrids 1 and 4, had the same nucleotide sequences.

The frequency of the chimerical gene formation using single-stranded DNA was much higher than that using the original sexual PCR method with double-stranded DNAs. Most likely, the probability of the homo-duplex formation in the annealing step of 1st PCR cycle using double-stranded gene fragments may be much higher than that of the hetero-duplex formation because of the nahH and xylE sequence divergence of 20%. On the other hand, when both the single-stranded nahH and the single-stranded xylE were digested by DNase I, nahH gene fragments could anneal only to fragmented xylE at the 1st PCR cycle. Although the elongation products could make homo-duplex at the 2nd or later cycles, the frequency of the hetero-duplex formation was expected to increase in the shuffling using single-stranded DNA.

The only difference between the methods using single-stranded DNA and double stranded DNA is the template DNA for fragmentation using DNase I or other appropriate methods. For single-stranded DNA preparation, the genes have to be cloned either in a phagemid vector or in a single-stranded DNA phage such as M13, and the single-stranded DNA have to be prepared from the filamentous phage particles. Although the shuffling using single-stranded DNAs needs one more step, it is worthwhile since nahH-xylE chimerical genes were formed much more efficiently than in the shuffling using double stranded DNA.

(2) Detailed Description of One of Many Possible Protocols of the Invention

(2-1) Preparation of ssDNAs

1. Clone two homologous genes separately in phagemid vectors (for example, pBluescript). The orientations of one gene with respect to the origin of the single-stranded DNA replication should be the same, while that of another gene should be opposite with respect to the origin of the single-stranded DNA replication. Then, the coding strand of one gene and the non-coding strand of another gene are synthesized and packaged in phage particles. In other words, single-stranded DNAs of the two homologous genes are complementary to each other.
2. Introduce the plasmids thus constructed into "male" *E. coli* such as JM109 (as the infection by single-stranded DNA phage requires F pili).
3. Inoculate a 1 ml culture of 2×YT medium supplemented with an appropriate antibiotics with a single JM109 transformant colony.
4. Grow the culture at 37° C. with shaking (e.g. rotary shaking at 250 rpm) to an optical density at 600 nm of 2.
5. Inoculate 25 ml of 2×YT containing an appropriate antibiotics in 250 ml Erlenmeyer flask with 0.5 ml of the above culture.
6. Incubate for 1 h with shaking at 37° C.
7. Infect with a helper phage at an m.o.i. (multiplicity of infection) of 10-20. Helper phages such as VCS-M13 (Stratagene) and M13KO7 (Pharmacia) are used for the rescue of ssDNA from phagemids. These helper phages can be prepared by propagating on a male *E. coli* strain.
8. Incubate overnight with shaking at 37° C.
9. Next day, harvest the cells by centrifuging at 12,000×g at 4° C. for 15 min.
10. Transfer the supernatant (containing phage particles) to a fresh tube. Do not introduce the pellet in the tube.
11. Spin the supernatant again, transfer the supernatant to a fresh tube.
12. Add 0.25 volume of phage precipitation solution to the supernatant. Leave on ice for at least 1 h, or overnight at 4° C.
13. Centrifuge at 12,000×g for 20 min at 4° C. In the presence of PEG, phage particles precipitate.
14. Remove the supernatant and resuspend the pellet in 400 ml of TE buffer, and transfer to a 1.5-ml tube.
15. Add one volume of TE-saturated phenol:chloroform:isoamyl alcohol (25:24:1) to the sample, vortex at least 1 min and centrifuge at 12,000×g for 5 min.
16. Transfer the upper phase (containing phagemid DNA) to a fresh tube without disturbing the interface. Repeat the organic solvent extraction until no visible material appears at the interface.
17. Add 0.5 volume (200 ml) of 7.5 M ammonium acetate plus two volumes (1.2 ml) of 100% ethanol. Mix and leave at −20° C. for 30 min to precipitate the phagemid DNA.
18. Centrifuge at 12,000×g for 5 min, remove the supernatant and carefully rinse the pellet with ice-cold 70% ethanol. If the pellet is disturbed, centrifuge again for 2 min. Drain the tube and dry the pellet under vacuum.
19. By agarose gel electrophoresis, two major bands corresponding to helper phage DNA and single-stranded DNA from phagemid are usually seen. A small amount of chromosomal DNA and RNA released by cell lysis may be present. Longer incubation during phagemid rescue increases the contamination of *E. coli* chromosomal DNA. Single-stranded DNA migrates faster than double stranded (ds) DNA of the same length. The presence of the helper phage DNA does not interfere with the following reactions.

(2-2) DNase I Treatment

1. Dilute 2 μg (or 3 pmol) of each DNA in 45 μl of TE buffer, and add 5 μl of 10× DNase I digestion buffer.
2. Incubate the solution at 15° C. for 5 min, then add 0.3 U of DNase I.
3. Incubate further for 2 min, then transfer to 90° C. and incubate for 10 min to terminate the reaction. The concentration of DNase I, the time and temperature for the reaction should be optimized as the digestion speed of DNase I is influenced by many factors including the nature of DNA. After DNase I treatment and subsequent incubation at 90° C., the brown precipitation may be produced. This is removed by centrifugation and then the supernatant is used for PCR.
4. Fragments in the size range of 40-100 bases are isolated from 2-3% low-melting-point agarose gel using QIAEX II gel extraction kit.
5. Resuspend the recovered DNA in 50 μl of TE buffer.

(2-3) PCR Reassembly and Amplification

1. Add to a 1.5 ml tube, 10 μl of 10×Pfu DNA polymerase buffer, 10 μl of dNTP mix, 10 μl of the purified fragments, 2.5 U of Pfu Turbo DNA polymerase and $H_2O$ to the total volume of 100 μl.
2. Perform PCR: 40 cycles of denaturation at 94° C. for 1 min, annealing at 56° C. for 1 min and elongation at 72° C. for 60+5 sec/cycle (the duration of elongation is increased by 5 sec after each cycle). This PCR amplification becomes difficult when the sizes of target genes are large, or the mean size of DNase I-cleave DNA is small. If the yield of the PCR products is low, the number of cycles in this PCR step should be increased.
3. Add to a new 1.5 ml tube, 1-5 μl of reassembled PCR product, 10 μl of 10×Pfu DNA polymerase buffer, 10 μl of dNTP mix, 2 μl of forward and reverse primers, 2.5 units of the Taq/Pfu DNA polymerase mixture and $H_2O$ to the total volume of 100 μl.
4. Perform PCR: 96° C. for 2 min followed by 25 cycles of 94° C. for 30 sec, 58° C. for 30 sec and 72° C. for 45+20 sec/cycle. This PCR amplification using primers seems to be inhibited when the concentrations of reassembled PCR products (i.e. the product of the first PCR without primers: step 2) are high. Check the concentrations of the first (step 2) and second (this step) PCR products on an agarose gel. If the second PCR amplification is not efficient, reduce the concentration of substrates (i.e. the product of the first PCR) in the second PCR.
5. Separate the PCR products on an agarose gel and recover a band corresponding to the size of the full length gene.
6. Purify the PCR products, subclone them and select desired mutants among transformants.

(2-4) Isolation of Thermally Stable C23Os

Thermally stable clones were screened from 750 colonies obtained by single-stranded DNA-based shuffling. After the treatment at 65° C. for 10 min, under which XylE (the xylE gene product, namely C23O produced from xylE) and NahH (the xylE gene product, namely C23O produced form nahH) were inactivated, 10 colonies exhibited the residual C23O activity, showing that they contain enzymes thermally more stable than the wild-type C23Os. The amino acid sequences of the thermally stable C23Os are shown in FIG. 6. Although the nucleotide sequences of all 10 clones were different, the deduced amino acid sequences of clones 120 and 942, clones 202 and 450, and clones 315 and 1527 were identical.

(2-5) Notes Concerning DNA Polymerases

Primer design is crucial in DNA shuffling. Primer length and sequence should carefully be determined for a successful amplification, cloning and gene expression. Follow general guidelines on the primer design for PCR cloning that are described in many textbooks. Sequences flanking the target gene can also be used for the primer design.

Taq DNA polymerase adds a single 3'-dA overhang to a blunt dsDNA template. For the cloning of such PCR products, linearized plasmid vectors containing single dT overhangs (T-vectors) were developed. The cloning efficiencies of the T-vectors, however, were variable. DNA polymerases with 3'→5' exonuclease (proofreading) activity remove mispaired nucleotides from 3' ends of dsDNA and generate blunt-end PCR products. The PCR products generated by these proofreading polymerases thus can be cloned into vectors by blunt-end ligation. However, blunt-end cloning of PCR products is less efficient than sticky-end cloning. Thus, it is advisable to introduce additional restriction sites at the 5' end of each of the primers. As amplification proceeds, these primers are incorporated into the PCR product. Thus, the PCR products can be digested by appropriate restriction enzymes to clone in an appropriate vector.

Taq polymerase lacks a 3'→5' exonuclease activity. In other words, it lacks the proofreading function of DNA replication, and thus exhibits a high rate of replication errors. This enzyme shows higher replication errors when the concentration of $MnCl_2$ in the reaction mixture increased, or when the concentration of one nucleotide was lower than those of other three nucleotides in the reaction mixture. By this reason, PCR with Taq polymerase was often used for the mutagenesis of genes. Pfu and Pfu Turbo DNA polymerases, on the other hand, show high fidelity of DNA replication. Zhao et al. (18) have reported that the using a proofreading DNA polymerase (Pfu or Pwo) in the reassembly step increased the frequency of active clones from the shuffling products. Therefor PCR with the proofreading DNA polymerase (Pfu Turbo) is used here to reduce the negative mutation.

The amplification by Pfu Turbo polymerase is not as powerful as that by Taq DNA polymerase. The replacement of Pfu Turbo polymerase by Taq DNA polymerase or by the mixture of Pfu Turbo and Taq polymerases often provides better results.

REFERENCES

The references cited above are shown below, the entire contents of each being hereby incorporated by reference.

1. Stemmer, W. P. C. (1994) DNA shuffling by random fragmentation and reassembly: in vitro recombination for molecular evolution. Proc. Natl. Acad. Sci. U.S.A., 91, 10747-10751.
2. Stemmer, W. P. C. (1994) Rapid evolution of a protein in vitro by DNA shuffling. Nature (London), 370, 389-391.
3. Shao, Z., Zhao, H., Giver, L., and Arnold, F. H. (1998) Random-priming in vitro recombination: an effective tool for directed evolution. Nucleic Acids Res., 26, 681-683.
4. Zhao, H., Giver, L., Shao, Z., Affholter, J. A., and Arnold, F. H. (1998) Molecular evolution by staggered extension process (StEP) in vitro recombination. Nat. Biotechnol., 16, 258-261.
5. Crameri, A., Whitehorn, E. A., Tate, E., and Stemmer, W. P. C. (1996) Improved green fluorescent protein by molecular evolution using DNA shuffling. Nat. Biotechnol., 14, 315-319.
6. Crameri, A., Dawes, G., Rodriguez, E., Jr., Silver, S., and Stemmer, W. P. C. (1997) Molecular evolution of an arsenate detoxification pathway by DNA shuffling. Nat. Biotechnol., 15, 436-438.

7. Moore, J. C. et al. (1997) Strategies for the in vitro evolution of protein function: Enzyme evolution by random recombination of improved sequences. J. Mol. Biol. 272, 336-347.

8. Yano, T., Oue, S., and Kagamiyama, H. (1998) Directed evolution of an aspartate aminotransferase with new substrate specificities. Proc. Natl. Acad. Sci. U.S.A., 95, 5511-5515.

9. Zhang, J. H., Dawes, G., and Stemmer, W. P. C. (1997) Directed evolution of a fucosidase from a galactosidase by DNA shuffling and screening. Proc. Natl. Acad. Sci. U.S.A., 94, 4504-4509.

10. Patten, P. A., Howard, R. J., and Stemmer, W. P. (1997) Applications of DNA shuffling to pharmaceuticals and vaccines. Curr. Opin. Biotechnol., 8, 724-733.

11. Crameri, A., Raillard, S. A., Bermudez, E., and Stemmer, W. P. C. (1998) DNA shuffling of a family of genes from diverse species accelerates directed evolution. Nature (London), 391, 288-291.

12. Harayama, S. (1998) Artificial evolution by DNA shuffling. Trends Biotechnol., 16, 76-82.

13. Kumamaru, T., Suenaga, H., Mitsuoka, M., Watanabe, T., and Furukawa, K. (1998) Enhanced degradation of polychlorinated biphenyls by directed evolution of biphenyl dioxygenase. Nat. Biotechnol., 16, 663-666.

14. Chang, C.-C., Chen, T. T., Cox, B. W., Dawes, G. N., Stemmer, W. P. C., Punnonen, J., and Patten, P. A. (1999) Evolution of a cytokine using DNA family shuffling. Nat. Biotechnol., 17, 793-797.

15. Hansson, L. O., B-Grob, R., Massoud, T., and Mannervik, B. (1999) Evolution of differential substrate specificities in Mu class glutathione transferases probed by DNA shuffling. J. Mol. Biol., 287, 265-276.

16. Kikuchi, M., Ohnishi, K., and Harayama, S. (1999) Novel family shuffling methods for the in vitro evolution of enzymes. Gene, 236, 159-167.

17. Kikuchi, M., Ohnishi, K., and Harayama, S. (2000) An effective family shuffling method using single-stranded DNA. Gene, 243, 133-137.

18. Zhao, H., and Arnold, F. H. (1997) Optimization of DNA shuffling for high fidelity recombination. Nucleic Acids Res., 25, 1307-1308.

While the invention has been described in detail and with reference to specific embodiments thereof, it will be apparent to one skilled in the art that various changes and modifications can be made therein without departing from the spirit and scope thereof.

What is claimed is:

1. A method for making libraries of hybrid polynucleotide molecules comprising the steps of:
   (i) selecting and separately cloning a first single-stranded polynucleotide comprising a coding strand of a first family gene;
   (ii) selecting and separately cloning a second single-stranded polynucleotide comprising a non-coding strand of a second family gene;
   (iii) fragmenting the first and second single stranded polynucleotides thereby forming polynucleotide fragments;
   (iv) incubating the polynucleotide fragments formed in step (iii) under conditions such that hybridization occurs to form heteroduplex molecules; and
   (v) conducting nucleotide elongation on the heteroduplex molecules, wherein said first and second single-stranded polynucleotide molecules are used as starting molecules, thereby providing said library of hybrid polynucleotide molecules.

2. The method of claim 1, wherein the first family gene is different from the second family gene and wherein the first single-stranded polynucleotide comprises at least one homologous sequence and at least one sequence which is heterologous to the second single-stranded polynucleotide.

3. The method of claims 1 or 2 wherein mutations are introduced into hybrid polynucleotide molecules.

4. The method of claim 2, wherein said homologous sequence is at least 15 bases.

5. The method of claim 1, wherein said cloning of said first single stranded polynucleotides in step (i) and said cloning of said second single stranded polynucleotides in step (ii) are performed by cloning said first and second single stranded polynucleotides using a phagemid vector or a single-stranded DNA phage vector.

6. The method of claim 1, wherein said cloning of said first single stranded polynucleotides in step (i) and said cloning of said second single stranded polynucleotides in step (ii) are performed by asymmetric PCR.

7. A method for making libraries of hybrid polynucleotide molecules, which comprises:
   (i) preparing and separately cloning two single stranded polynucleotide molecules comprising sequences which are complementary to each other,
   (ii) fragmenting the two single-stranded polynucleotide molecules,
   (iii) incubating the fragmented molecules under conditions such that hybridization of fragmented polynucleotide molecules occurs and de novo polynucleotide synthesis on the hybridized molecules occurs to produce elongated double stranded polynucleotide molecules,
   (iv) denaturing the elongated double stranded polynucleotide molecules produced in step (iii) into single-stranded polynucleotide molecules,
   (v) incubating the single-stranded polynucleotide molecules produced in step (iv) under conditions such that hybridization of single-stranded polynucleotide molecules occurs and de novo polynucleotide synthesis of hybridized molecules occurs, and
   (vi) repeating at least two further cycles of (iv) and (v), thereby providing said library of hybrid polynucleotide molecules.

8. The method of claims 1 or 7, wherein at least one of the two single-stranded polynucleotides is fragmented randomly.

9. The methods of claims 1 or 7, wherein both of the two single-stranded polynucleotides is fragmented randomly.

10. The method of claims 1 or 7, wherein mutations are introduced into at least one first and second single-stranded polynucleotides prior to production of heteroduplex molecules.

11. The method of claims 1 or 7, wherein mutations are introduced into both of the first and second single-stranded polynucleotides prior to production of the heteroduplex molecules.

12. The method of claim 7, wherein said cloning of said two single stranded polynucleotide molecules in step (i) is performed by cloning said two single stranded polynucleotides using a phagemid vector or a single-stranded DNA phage vector.

13. The method of claim 7, wherein said cloning of said two single stranded polynucleotide molecules in step (i) is performed by asymmetric PCR.

* * * * *

UNITED STATES PATENT AND TRADEMARK OFFICE
CERTIFICATE OF CORRECTION

| | | |
|---|---|---|
| PATENT NO. | : 7,662,551 B2 | Page 1 of 1 |
| APPLICATION NO. | : 10/299362 | |
| DATED | : February 16, 2010 | |
| INVENTOR(S) | : Harayama et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 937 days.

Signed and Sealed this

Thirtieth Day of November, 2010

David J. Kappos
*Director of the United States Patent and Trademark Office*